(12) United States Patent
Mandella et al.

(10) Patent No.: US 6,252,666 B1
(45) Date of Patent: Jun. 26, 2001

(54) METHOD AND APPARATUS FOR PERFORMING OPTICAL COHERENCE-DOMAIN REFLECTOMETRY AND IMAGING THROUGH A SCATTERING MEDIUM EMPLOYING A POWER-EFFICIENT INTERFEROMETER

(75) Inventors: Michael J. Mandella, Cupertino; Mark H. Garrett, Morgan Hill; Gordon S. Kino, Stanford, all of CA (US)

(73) Assignee: Optreal Biopsy Technologies, Inc., Santa Clara, CA (US)

( * ) Notice: Subject to any disclaimer, the term of this patent is extended or adjusted under 35 U.S.C. 154(b) by 0 days.

(21) Appl. No.: 09/540,298

(22) Filed: Mar. 31, 2000

Related U.S. Application Data

(62) Division of application No. 09/042,205, filed on Mar. 13, 1998.

(51) Int. Cl.⁷ ............................................. G01B 9/02

(52) U.S. Cl. .................. 356/479; 356/497; 356/485; 356/492

(58) Field of Search .................... 356/479, 497, 356/487, 492, 491, 493

(56) References Cited

U.S. PATENT DOCUMENTS

| | | | |
|---|---|---|---|
| 5,013,907 | 5/1991 | Bateman | 250/227.12 |
| 5,202,745 | * 4/1993 | Sorin et al. | 356/73.1 |
| 5,268,738 | 12/1993 | Baney et al. | 356/345 |

OTHER PUBLICATIONS

Fujimoto, et al., Optical Coherence Tomography, Optics & Photonics News, Jan. 2000, pp. 24–31.

Rollins et al., Real–time in vivo imaging of human gastrointestinal ultrastructure by use of endoscopic optical coherence tomography with a novel efficient interferometer design, Optics Letters, 24(19), pp. 1358–1360, 1999.

Izatt, et al., Optical Coherence Tomography and Microscopy in Gastrointestinal Tissues, IEEE Journal of Selected Topics in Quantum Electronics, 2(4), pp. 1017–1028, 1996.

Drexler, et al., Subcellular optical coherence tomography with a kerr lens mode–locked Ti:$Al_2O_3$ laser, Proceedings of The SPIE Conference on Coherence Domain Optical Methods in Biomedical Science and Clinical Applications III, San Jose, California, Jan. 1999, pp. 216–223.

Wang, et al., High Speed, full field optical coherence microscopy, Proceedings of The SPIE Conference on Coherence Domain Optical Methods in Biomedical Science and Clinical Applications III, San Jose, California, Jan. 1999, pp. 204–212.

(List continued on next page.)

Primary Examiner—Frank G. Font
Assistant Examiner—Andrew H. Lee
(74) Attorney, Agent, or Firm—Lumen

(57) ABSTRACT

An apparatus and method for performing optical coherence domain reflectometry. The apparatus preferably includes a single output light source to illuminate a sample with a probe beam and to provide a reference beam. The reference beam is routed into a long arm of an interferometer by a polarizing beamsplitter. A reflected beam is collected from the sample. A 90° double pass polarization rotation element located between the light source and the sample renders the polarizations of the probe beam and reflected beam orthogonal. The polarizing beamsplitter routes the reflected beam into a short arm of the interferometer. The interferometer combines the reference beam and the reflected beam such that coherent interference occurs between the beams. The apparatus ensures that all of the reflected beam contributes to the interference, resulting in a high signal to noise ratio.

33 Claims, 16 Drawing Sheets

OTHER PUBLICATIONS

Morgner, et al., Spectroscopic optical coherence tomography, Optics Letters, 25(2), pp. 111–113, 2000.

Drexler, et al., In vivo ultrahigh–resolution optical coherence tomography, Optics Letters, 21(17), pp. 1221–1223, 1999.

Bouma, et al., Power–efficient nonreciprocal interferometer and linear–scanning fiber–optic catheter for optical coherence tomography, Optics Letters, 24(8), pp. 531–533, 1999.

Schmitt, et al., Cross–polarized backscatter in optical coherence tomography of biological tissue, Optics Letters, 23(13), pp. 1060–1062, 1998.

Park, et al., High resolution optical ranging system, Applied Optics, 20(14), pp. 2389–2394, 1981.

* cited by examiner

Fig. 3  Probe Beam
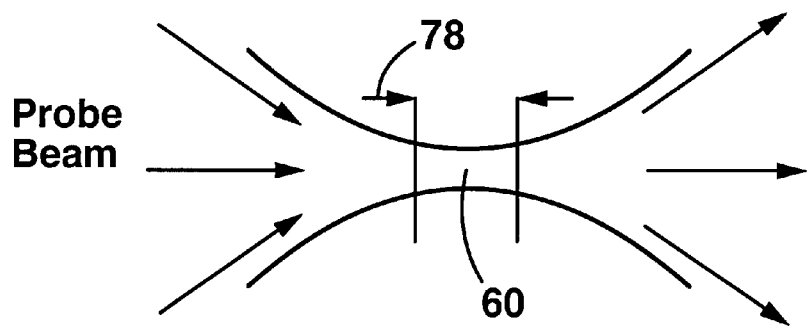
Fig. 4 Prior Art  Probe Beam
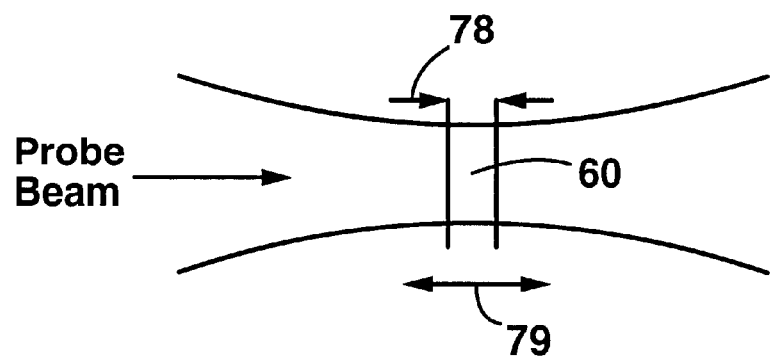

METHOD AND APPARATUS FOR PERFORMING OPTICAL COHERENCE-DOMAIN REFLECTOMETRY AND IMAGING THROUGH A SCATTERING MEDIUM EMPLOYING A POWER-EFFICIENT INTERFEROMETER

CROSS-REFERENCE TO RELATED APPLICATIONS

This application is a divisional of copending U.S. patent application 09/042,205 filed Mar. 13, 1998 (still pending), which is herein incorporated by reference.

FIELD OF THE INVENTION

This invention relates generally to confocal microscopy and optical coherence domain reflectometry (OCDR). More specifically, it relates to devices for measuring optical reflectance and imaging through a thickness of biological tissue.

BACKGROUND OF THE INVENTION

There are a number of applications for techniques for optical measurement through light scattering materials. Most notably, such measurements can be performed through biological tissues and therefore can be used for noninvasive medical diagnostic tests. Cancer tissue and healthy tissue, for example, can be distinguished by means of different optical properties. Scanning the optical measurement can yield high contrast and high magnification images of biological tissues. For example, imaging techniques could be used to examine plaque on the interior walls of arteries and vessels or other small biological structures. Related applications extend to the examination and troubleshooting of integrated optical circuits, fiber optic devices, and semiconductor structures. All these applications require that the measuring technique have a relatively high spatial resolution (microns or tens of microns), high sensitivity, and low noise.

Optical time domain reflectometry (OTDR) and optical frequency domain reflectometry (OFDR) are techniques which are used to examine optical systems and are generally not capable of performing high resolution measurements through a light scattering material. For example, these methods are generally designed for finding and locating (to within 1 meter) flaws in a fiber optic system.

Optical coherence domain reflectometry (OCDR) is a technique which has been used to image an object within or behind light scattering media. The technique uses short coherence length light (typically with a coherence length of about 10–100 microns) to illuminate the object. Light reflected from a region of interest within the object is combined with a coherent reference beam. Interference occurs between the two beams only when the reference beam and reflected beam have traveled the same distance. This allows the OCDR to discriminate against light scattered from outside the region of interest.

FIG. 1 shows a typical OCDR setup similar to ones disclosed in several U.S. patents (U.S. Pat. Nos. 5,465,147, 5,459,570, and 5,321,501 issued to Swanson et al., U.S. Pat. Nos. 5,291,267, 5,365,335, and 5,202,745 issued to Sorin et al). FIG. 1 shows the device made with fiber optic components, but OCDR devices can also be made with bulk optical components. Light having a short coherence length $l_c$ (given by $l_c = C/\Delta f$, where $\Delta f$ is the spectral bandwidth) is produced by a light source 20 and travels through a 50/50 coupler 22 where it is divided into two paths.

One path goes to the sample 24 to be analyzed and the other path goes to a movable reference mirror 26. Extra fiber length in the reference path is shown as fiber loop 31. The probe beam reflected from the sample 24 and reference beam reflected from the reference mirror 26 are combined at the coupler 22 and sent to a detector 28. The optical paths traversed by the reflected probe beam and reference beam are matched to within one coherence length such that coherent interference can occur upon recombination at the coupler.

A phase modulator 30 (such as a piezoelectric fiber stretcher) produces sideband frequencies in the probe beam which produce a temporal interference pattern (beats) when recombined with the reference beam. The detector 28 measures the amplitude of the beats. The amplitude of the detected interference signal is a measure of the amount of light scattered from within a coherence gate interval 32 inside the sample 24 that provides equal path lengths for the probe and reference beams. Interference is produced only for light scattered from the sample 24 which has traveled the same distance (to within approximately one coherence length) as light reflected from the mirror 26. The coherence gate interval 32 has a width of approximately one coherence length. This feature of OCDR allows the apparatus to discriminate against light which is scattered from outside the coherence gate interval 32, and which is usually incoherent compared to the reference beam. This discrimination (a 'coherence gate') results in improved sensitivity of the device.

One negative consequence of the geometry of FIG. 1 is that 50% of the light reflected from the sample 24 is lost. On its return trip through the coupler 22, half the reflected probe beam enters the light source 20 and does not enter the detector 28. This is undesired because it decreases the signal to noise ratio of the device and results in a more powerful light source being required. Another negative feature of the device of FIG. 1 is that it requires the use of a moving mirror to scan longitudinally in and out of the sample 24. The use of a moving mechanical mirror is a disadvantage because moving mechanical parts often have alignment and reliability problems.

Another disadvantage of the device of FIG. 1 is the requirement for a large depth of focus of the probe beam in sample 24. A large depth of focus is necessary to allow longitudinal scanning of the coherence gate interval 32 while maintaining the coherence gate interval in the region of the beam having a reasonably small spot size. This requirement increases the minimum spot size of the beam, and thus limits the spatial resolution of the device when acquiring images.

A further disadvantage of the device of FIG. 1 is the long integration time typically necessary for each measurement point (pixel) when acquiring an image. This is due to the low power of the backreflected signal when imaging deep within a scattering medium. Under these conditions, the slow acquisition time does not allow in-vivo imaging of live tissue which is usually in motion.

U.S. Pat. No. 5,291,267 to Sorin et al. discloses a technique for OCDR which uses the light source as a light amplifier in order to boost the reflected signal from the sample. Light reflected from the sample is returned through the light source in a reverse direction and is amplified as it passes through. However, Sorin's device requires a coupler in the light path between the source and sample and so necessarily wastes 50% of the light reflected from the sample. In other words, only 50% of the light reflected by the sample is amplified and contributes to the interference signal. Consequently, Sorin's device produces less than optimum signal to noise ratio resulting in less accurate measurements.

OBJECTS AND ADVANTAGES OF TE INVENTION

Accordingly, it is a primary object of the present invention to provide a method and apparatus for reflectance measurements through light scattering materials that:
1) requires fewer active components than prior art techniques;
2) utilizes all the light reflected from the sample;
3) provides an improved signal to noise ratio compared to prior art techniques;
4) is able to scan deep into scattering materials such as biological tissue;
5) is able to produce vertical-section, horizontal-section, or three dimensional images;
6) has short data acquisition times for real-time in-vivo imaging of live tissue;
7) has high spatial resolution thus enabling the imaging of microscopic structures such as biological structures; and
8) is easy and inexpensive to manufacture.

These and other objects and advantages will be apparent upon consideration of the following description and accompanying drawings.

SUMMARY

The invention presents a method and apparatus for performing optical coherence domain reflectometry on a sample of light scattering media. In a preferred embodiment, the apparatus includes a single output light source for illuminating a sample, a polarizing beamsplitter, a 90° double pass polarization rotation element, and an interferometer having a short arm and a long arm. The sample is illuminated with a probe beam emitted from the light source. The probe beam travels to the sample along a light path. The polarizing beamsplitter is positioned to split off a reference beam from the probe beam and to route the reference beam into the long arm of the interferometer.

The probe beam reflects from the sample, producing a reflected beam. The polarization rotation element is located between the light source and sample such that the reflected beam and the probe beam have orthogonal polarizations. The reflected beam is reflected from the polarizing beamsplitter and routed into the short arm of the interferometer. The arms of the interferometer have optical path lengths selected to provide coherence between the reference beam and the reflected beam.

According to an alternative embodiment, the apparatus includes a single output light source for illuminating the sample, a first beamsplitter, a second polarizing beamsplitter, a 90° double pass polarization rotation element, and an interferometer having a short arm and a long arm. The sample is illuminated with a probe beam emitted from the light source. The probe beam travels to the sample along a light path. The first beamsplitter splits off a reference beam from the probe beam and routes the reference beam into the long arm of the interferometer.

The probe beam reflects from the sample, producing a reflected beam. The polarization rotation element is located between the light source and the sample such that the reflected beam and the probe beam have orthogonal polarizations. The second polarizing beamsplitter is located such that the reflected beam is separated from the probe beam and routed into the short arm of the interferometer. The reference beam and the reflected beam are combined at the output of the interferometer, where coherent interference occurs. The lengths of the long arm and short arm are selected to provide coherence between the reference beam and the reflected beam.

The first beamsplitter is preferably a polarizing beamsplitter so that the probe beam and the reference beam have orthogonal polarizations. The light source can also be polarized. In this case, if the first beamsplitter is a polarizing beamsplitter, then the amount of optical power routed into the reference beam can be controlled by adjusting the orientation of the first beamsplitter with respect to the polarization of the light source.

The interference is modulated by modulating the phase or frequency of the reference beam or the probe beam with a phase modulator. The phase modulator can be located within one arm of the interferometer or in the light path. Preferably, the phase modulator is driven sinusoidally. One arm of the interferometer can include a variable optical attenuator to control the amount of optical power in the reference beam. The light path between the light source and the sample can comprise an optical fiber. The light source preferably has a coherence length of less than 3000 microns. The light source also preferably produces light in the wavelength range of 0.8 to 1.6 microns, over which range biological tissues are particularly transparent.

The light path preferably includes a transverse scanning mechanism for scanning the probe beam within the sample. Such a scanning mechanism can have a micromachined scanning mirror. A longitudinal scanning mechanism can also be provided to scan in a direction parallel to the probe beam. Scanning allows the apparatus to create images. Longitudinal scanning in the direction of the probe beam axis, along with scanning in a direction perpendicular to the axis, provides the possibility of obtaining an image of a vertical cross section of the sample.

The light path can also have a lens for focusing the probe beam to a small spot within the sample. The lens preferably has a numerical aperture in the range of 0.4 to 1.4. The interferometer is preferably a Mach-Zehnder type made of two unequal lengths of optical fiber coupled on each end by fiber optic couplers.

In an alternative embodiment, the apparatus includes a two output light source, a phase modulator, an interferometer having unequal path lengths (arms), and an optical detector. The light source emits a probe beam from a probe aperture and a reference beam from a reference aperture. The interferometer is disposed in optical communication with the reference aperture so that the reference beam travels directly into the interferometer.

The probe beam travels to the sample through the phase modulator which is located between the light source and the sample. The probe beam reflects from the sample, producing a reflected beam. The reflected beam travels back to the light source from the sample. The light source is also preferably an amplifier and so amplifies the reflected beam. The reflected beam and reference beam are combined inside the light source and pass into the interferometer. The light source is located such that the reflected beam is collinear with the reference beam at the reference aperture.

The interferometer has a beamsplitter for splitting the reference beam and reflected beam into arms of unequal lengths. The lengths of the interferometer arms are selected to restore the optical coherence between the reference beam and the reflected beam. Preferably, one arm of the interferometer has a variable optical path length device for adjusting the path length difference between the arms. The phase modulator is driven by an oscillator such that the reference beam and reflected beam have different spectral characteristics. Therefore, the reference beam and the reflected beam produce a temporal interference pattern at the output of the interferometer. The optical detector is positioned in optical communication with the interferometer to detect the temporal interference.

The apparatus can also have a 90° double pass polarization rotation element located in the light path such that the reflected beam has a polarization orthogonal to the reference beam. This allows the reference beam and reflected beam to be separated into the different arms of the interferometer. One arm of the interferometer can have a 90° polarization rotator which renders the polarizations of the reference and reflected probe beams parallel before being recombined.

In the case where the light path has a 90° polarization rotation element, the interferometer can be a length of birefringent optical fiber oriented such that the reference beam experiences a higher index of refraction than the reflected beam. Further, if the birefringent optical fiber has a non-zero coefficient of birefringence, then the optical path length difference between the interferometer arms can be controlled by controlling the temperature of the birefringent fiber.

DESCRIPTION OF THE FIGURES

FIG. 3 is a close-up view of a focal point within a sample medium.

FIG. 4 is a close-up view of a focal point of a prior art apparatus.

DETAILED DESCRIPTION

Figure 2:
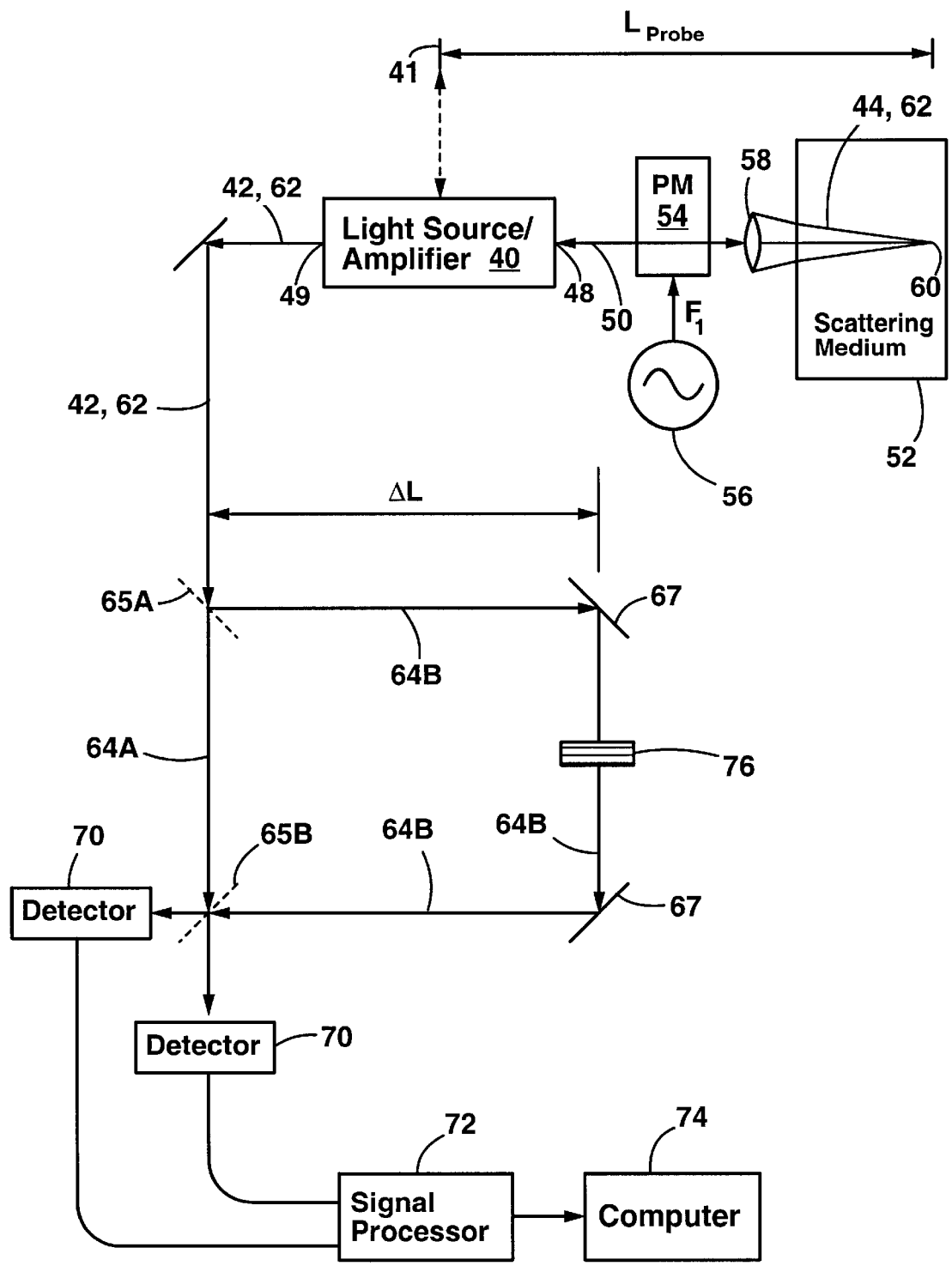
FIG. 2 shows an optical coherence domain reflectometer made with bulk optical components according to a first embodiment of the present invention.

FIG. 2 shows a first embodiment of an apparatus for performing optical coherence domain reflectometry on a sample of light scattering media. In the first embodiment, the apparatus is constructed from bulk optical components. A two output light source 40 illuminates a sample 52 with a probe beam 44. The sample comprises a light scattering medium such as biological tissue. The light source emits the probe beam 44 from a probe aperture 48. The light source also emits a reference beam 42 from a reference aperture 49. The reference beam 42 is emitted directly into an interferometer having a short arm 64A and a long arm 64B. The interferometer shown is a Mach-Zehnder type, but other types can be used as well. The interferometer outputs light into two optical detectors 70 which detect interference. The detectors output to a signal processor 72 and a computer 74.

The light source 40 preferably has a relatively short coherence length in the range of 30 to 3000 microns. The reference beam 42 and the probe beam 44 are counterpropagating. Proper choice of a light source for a given application involves selecting a proper coherence length and wavelength which optimizes the sensitivity of the device. The reference beam 42 and the probe beam 44 are coherent with respect to one another and travel in opposite directions. The light source 40 of the embodiment of FIG. 2 should be a two output light source to provide the counterpropagating reference beam and probe beam. The light source 40 may be, for example, a semiconductor optical amplifier or fiber optical amplifier which emits light from front and rear apertures. In cases where higher probe beam power is desired, the light source 40 may be a semiconductor laser or fiber laser which emits from front and rear cavity reflectors.

The probe beam 44 exits the probe aperture 48 and travels along a light path 50 to the sample 52. The light path 50 passes through a phase modulator 54 which varies the phase of the probe beam 44 at a predetermined frequency $F_1$. The phase modulator is electrically driven by an oscillator 56. Preferably, the phase of the probe beam 44 is varied in a sinusoidal fashion, although other modulation waveforms can be used. The phase modulator can be a piezoelectric fiber stretcher (in the case where optical fiber components are used), or electrooptic crystal, for example. Other methods well known in the art of light modulation can also be used. A lens assembly 58 focuses the probe beam 44 to a focal point 60 within the sample 52.

A portion of the light scattered or reflected by the sample 52 at the focal point 60 is collected by the lens 58 and travels in a direction exactly opposite the original probe beam 44. This reflected light comprises a reflected probe beam 62. The reflected probe beam 62 thus travels back through the phase modulator 54 and through the light source/amplifier 40. The reflected probe beam 62 is coherently amplified as it passes through the light source/amplifier 40. In this way, the light source/amplifier performs two functions: light source and light amplification. The amplified, reflected probe beam emerges from the reference aperture 49 of the light source/amplifier traveling collinear and parallel with the reference beam 42.

The two beams then enter the interferometer having two arms 64A, 64B of different path lengths. In the particular embodiment of FIG. 2, the interferometer is comprised of 50/50 beamsplitters 65A, 65B and mirrors 67. The path length difference between the two optical paths in the interferometer is equal to twice the length ΔL. Length ΔL is equal to the distance between beamsplitter 65A and mirror 67. When the reflected probe beam 62 arrives at the reference aperture 49, it has traveled further than the reference beam by a distance equal to twice the length $L_{probe}$. It is noted that length $L_{probe}$ is measured from the center 41 of the light source 40 to the focal point 60 inside the sample 52. The apparatus is designed such that 2ΔL is equal to $2L_{probe}$ to within approximately one optical coherence length of the light source 40. Expressed mathematically, this relationship is:

$$|2\Delta L - 2L_{probe}| < L_c,$$

where $L_c$ is the coherence length of the probe and reference beams. Coherent interference between the reference beam 42 and reflected probe beam 62 occurs at beamsplitter 65B when this condition is satisfied. The portion of the reference beam 42 which travels through the long arm 64B of the interferometer interferes with the portion of the reflected probe beam 62 which travels through the short arm 64A of the interferometer.

The output of the interferometer is monitored by the two optical detectors 70. The detectors measure the light intensity and are preferably high-speed photodiodes such as PIN photodiodes or avalanche photodiodes. The signal received by the detectors 70 is a temporal fluctuation in light intensity (a temporal interference pattern) whose frequency is determined by the driving frequency $F_1$ of the phase modulator 54. For example, if the phase modulator 54 is driven sinusoidally at frequency $F_1$, then the detectors 70 will output a signal at frequency $F_1$. The amplitude of the detector signal at $F_1$ is determined by the amount of light reflected at the focal point 60. Therefore, the detector output amplitude at $F_1$ is a measure of the reflectance of the sample 52 at the focal point 60.

High-pass filters located within the signal processing unit 72 may be necessary to accurately measure the amplitude of $F_1$. The signal processor may also perform analog to digital conversion and output to the computer 74, where reflectance measurements are stored. If the focal point 60 is scanned throughout the sample 52, then two dimensional or three dimensional images of the reflectance of the interior of the sample 52 can be created from the time-varying $F_1$ signal. These images can be used to diagnose cancer or other internal medical conditions.

If the optical path between the probe aperture 48 and lens assembly is fixed, then at least one arm of the interferometer should have a variable optical path length to provide a mechanism for adjusting length ΔL. For example, a variable optical path length can be provided by moving mirrors 67, or by inserting a variable optical delay device into one of the arms of the interferometer. The variable optical path length can then be adjusted until coherent interference occurs at the beamsplitter 65B and detectors 70.

Preferably, the phase modulator 54 is located in the light path 50 between the light source 40 and sample 52 to modulate the probe beam 44. However, the reflected probe beam 62 can also be modulated by locating the phase modulator 54 in the short arm 64A of the interferometer. Phase modulation of the reference beam 42 will also modulate the temporal interference. This can be accomplished by locating the phase modulator 54 in the long arm 64B of the interferometer. Therefore, the present invention can have the phase modulator 54 located within the light path 50 or within either arm 64A, 64B of the interferometer.

It is noted that the portion of the reference beam 42 which travels through the short arm 64A does not interfere with the portion of the reflected probe beam 62 which travels through the long arm 64B. This non-interfering light does not contribute to the temporal interference signal and thus is noise in the system. Therefore, locating the phase modulator 54 in either interferometer arm 64A, 64B may decrease the signal-to-noise ratio of the detector signal.

The signal-to-noise ratio of the signal output by detector 70 can be maximized by including an optical attenuator 76 in the long arm 64B (the reference path) of the interferometer. This is because the reference beam 42 will (for most embodiments) be much brighter than the reflected probe beam 62. The reference beam may contain a component of noise known as relative intensity noise (RIN) produced by the light source. The noise due to RIN is proportional to the signal strength. An alternative method of minimizing the effects of noise is the method of balanced detection. Reference can be made to Takada et al., Applied Physics Letters, 59, page 143, 1991.

A major advantage of the present invention over the use of a standard confocal microscope is that the signal to noise ratio of the signal output by detector 70 can be maximized by using as strong a reference signal as possible. If the reflected probe beam is of amplitude A, and the reference beam of amplitude B, the detected signal will be proportional to:

$$|(A+B)|^2 = |A|^2 + 2|AB| + |B|^2.$$

Since one of the beams is phase modulated the only signal of frequency F1 is the 2AB term. In the case of deep tissue imaging, then $|A| << |B|$. Thus, the detected output is proportional to the amplitude of the reference signal as well as that of the reflected probe, and it is advantageous to use as strong a reference signal as possible. This result should be contrasted with that for the standard confocal microscope, where the detected output of the relatively weak reflected probe beam is proportional to $|A|^2$. Ideally, an input probe beam of about the same amplitude as the input reference beam is used so as to utilize the available power as efficiently as possible. An adjustable optical attenuator 76 may be included in the long arm 64B (the reference path) to avoid saturation of the detector or to attenuate the reference beam if the light source is noisy.

FIG. 3 shows a close-up view of the focal point 60 within the sample. The coherence length of the light source 40 and the length of the long arm 64B of the interferometer establish a coherence gate interval 78 located about the focal point 60. Probe beam light reflects from within the coherence gate interval 78 and travels the same distance (to within a coherence length) as the reference beam light 42 upon arrival at the beamsplitter 65B and detectors 70. Therefore, the coherence gate interval 78 can be moved back and forth in the probe beam path by changing slightly the length of the long arm 64B or the short arm 64A.

The width of the coherence gate interval 78 can be increased (or decreased) by increasing (or decreasing) the coherence length of the light source 40. Preferably, the coherence gate interval 78 is centered about the focal point 60 and is fixed with respect to the focal point. Longitudinal scanning (in and out of the sample 52) of the focal point 60 and coherence gate interval 78 is achieved by causing relative motion between the lens assembly 58 and the sample 52. In this way the focal point 60 always lies within the coherence gate interval 78 during scanning of the focal point both in transverse and longitudinal directions. Preferably, the coherence gate interval 78 is not used to define the longitudinal image resolution, as is done in the cited prior art devices. Also, unlike in prior art devices, the apparatus does not scan the coherence gate interval through a fixed focal point having a relatively large depth of field to accomplish longitudinal scanning of the image. Instead, the apparatus uses the coherence gate only for reducing the "glare" or scattered photon noise coming from regions near the sample surface. This, in combination with using a high numerical aperture focusing lens, improves image contrast and allows a higher transverse spatial resolution than is obtained in the prior art devices.

The longitudinal and transverse resolution are determined by the depth of focus and spot diameter, respectively, of the focal point 60. Using a lens assembly 58 having a high numerical aperture results in a small spot diameter and shorter depth of focus, thereby increasing both the longitudinal and transverse spatial resolutions. Preferably, the lens assembly 58 has a numerical aperture in the range of 0.4 to 1.4. In the case of a high numerical aperture lens assembly, a short coherence length laser used as the light source could provide a coherence gate width sufficient to improve the signal-to-noise ratio of the device provided that the coherence length is less than the imaging depth. For example, in order to gain an improvement in signal-to-noise performance, the coherence length does not have to be 10 to 30 microns as used for z-scanning in prior art optical coherence detection imaging systems employing low numerical aperture focusing lenses. Instead, high power and inexpensive diode lasers having coherence lengths of about 100 to 1000 microns may be used. This increases the signal-to-noise ratio while reducing cost.

Referring again to FIG. 2, the signal processor 72 and computer 74 convert the amplitude of the interference signal produced by the detectors 70 into a reflectance value for the location of the focal point 60. The focal point 60 and coherence gate interval (which are preferably fixed with respect to one another) can be scanned throughout the sample 52 to produce a three dimensional image of the reflectance of the sample interior. Therefore, although the apparatus of FIG. 2 only measures the reflectance at the focal point 60, the focal point 60 can be scanned to produce three dimensional images, or two dimensional images in any plane. For example, vertical-section or horizontal section images can be obtained.

Figure 1:
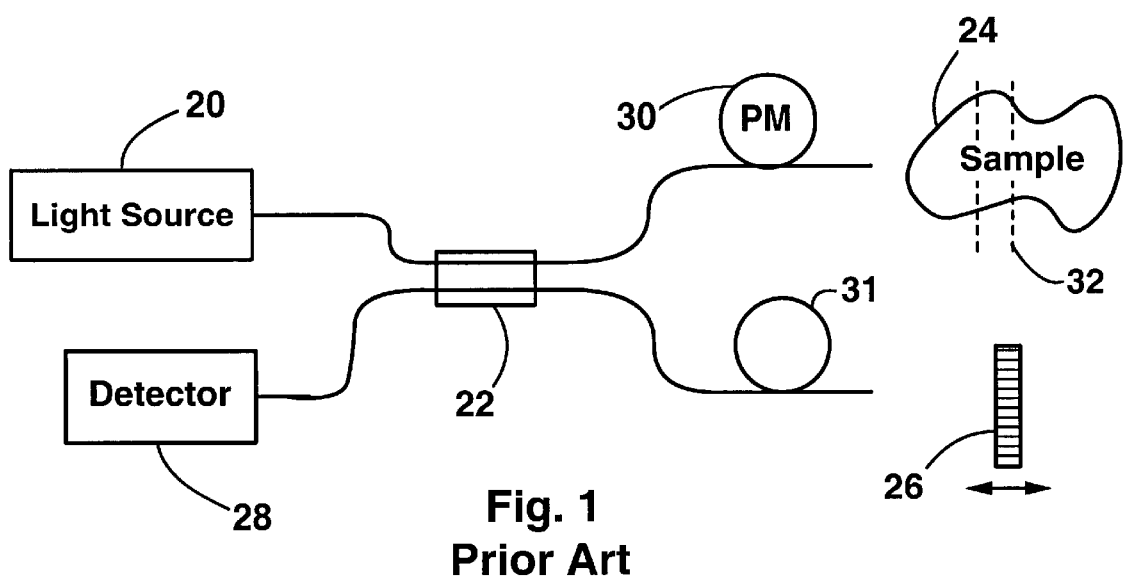
FIG. 1 shows a prior art optical coherence domain reflectometer.

FIG. 4 shows a close-up of the focal point 60 of a typical prior art OCDR device. Here, the coherence gate interval 78 is short compared to the 'length' of the focal point. The long focal point is a result of using a low numerical aperture lens assembly. Scanning parallel with the probe beam is performed by moving longitudinally the coherence gate interval 78 while the focal point 60 remains fixed. This is done by moving the scanning reference mirror 26 of FIG. 1. It is noted that the low numerical aperture of the lens assembly used in the prior art embodiment of FIG. 4 results in a lower transverse spatial resolution due to larger focus spot size (i.e. larger focus 'waist').

Figure 5A:
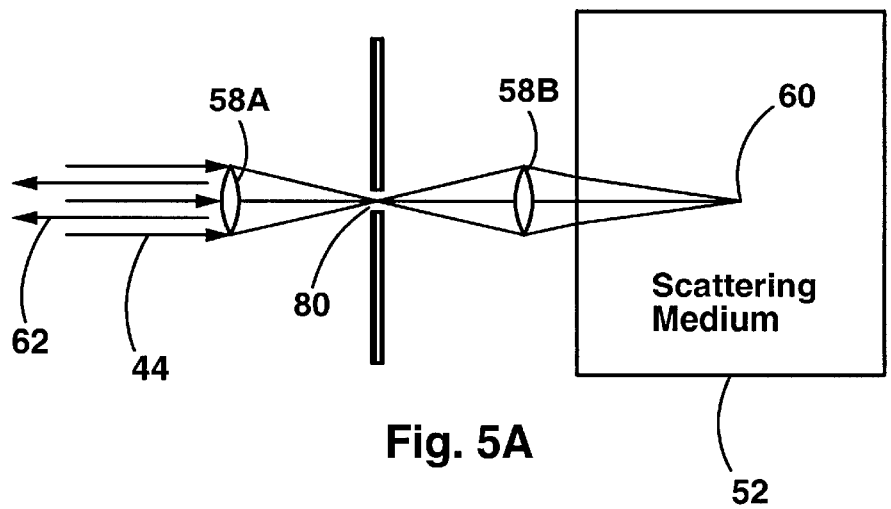
FIG. 5A shows a spatial filter which can be used in conjunction with a reflectometer according to the present invention.

Preferably, the light path 50 between the light source 40 and the sample 52 includes a confocal microscopy apparatus or, equivalently, a spatial frequency filter. FIG. 5A shows such an apparatus, which is well known in the art of optics. The probe beam 44 and reflected probe beam 62 are focused by lenses 58A, 58B and pass through a small aperture 80. The aperture 80 helps to further discriminate against probe beam light which did not reflect from the focal point 60. This improves the accuracy of the reflectivity measurement of the focal point 60. It is known in the art of confocal microscopy that the end of an optical fiber can function as the aperture of a spatial filter.

The advantage of using a high numerical-aperture lens 58B in the confocal lens assembly of FIG. 5A is that it can provide a very short range definition. For example, this range definition can be about 5 microns when lens 58B has a numerical aperture greater than 1 at a wavelength of 1.3 microns. This makes it possible to obtain good images of a vertical cross section of tissue. However, if a confocal microscope were used alone, the glare from tissue nearer to the lens 58B than the focus would tend to give a response much like that shown as the confocal microscope response in FIG. 5B. This problem can be obviated by combining the confocal microscope response and coherence gate response.

Figure 5B:
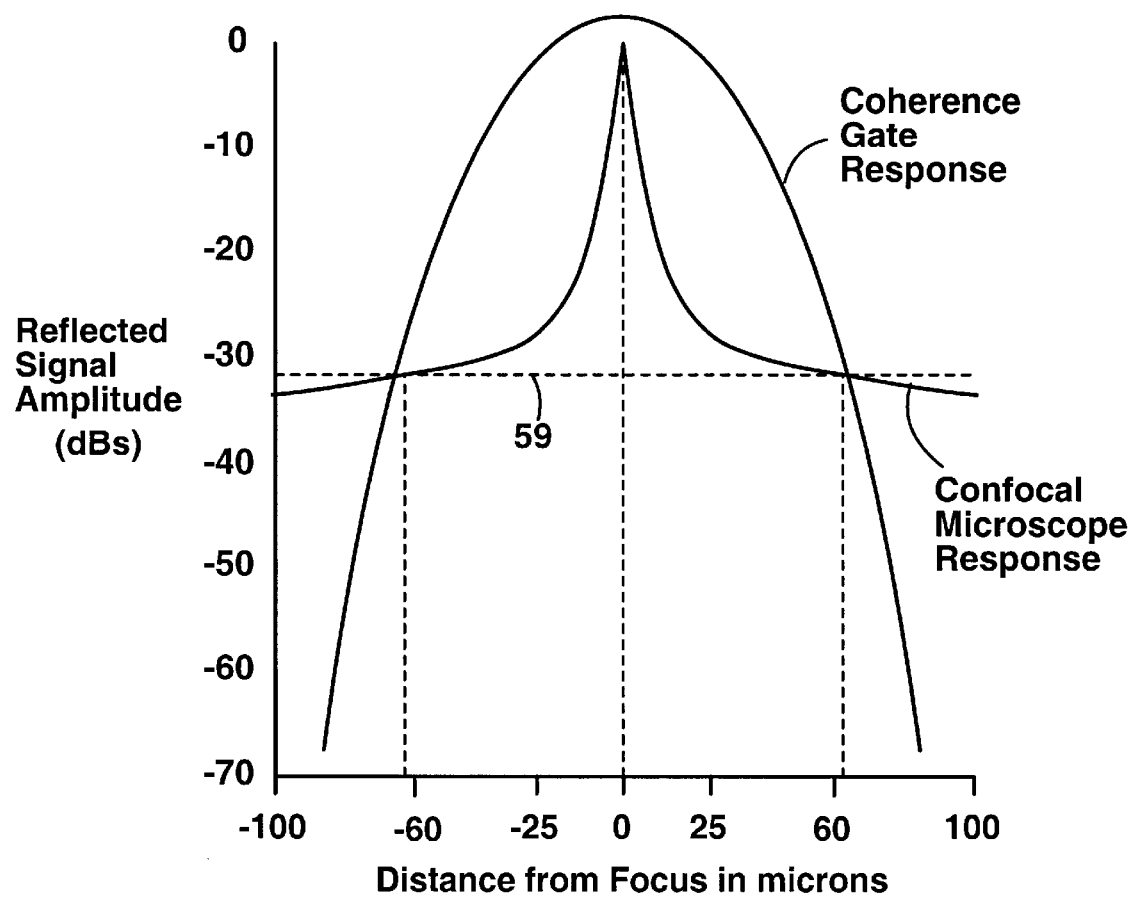
FIG. 5B shows a graph which illustrates the signal response from a coherence gate and from a confocal microscope.

In the example shown in FIG. 5B, the response of the coherence gate is wider than the confocal microscope response above the −33 dB level indicated at 59. The response obtained from a combined confocal/coherence gate response will be mainly from a region within about 60 microns from the focus. Outside of this range, the response follows that of the coherence gate, and falls off far more rapidly than the confocal microscope response. In this case, although the coherence gate might be of the order of 100 microns wide, the range definition of the high numerical-aperture lens can still be obtained.

The reflectometer of the first embodiment is able to measure deep into the sample 52 because the optical system uses both a confocal microscope assembly and coherence gating, which provides high signal-to-noise performance. Even if the coherence length is as long as a few millimeters, the system is far more sensitive than a standard microscope because it obtains an output signal linearly proportional to the amplitude A of the weak reflected probe beam rather than the square of the amplitude, $A^2$.

The reflectometer also ensures that nearly all the probe beam 44 (minus small optical losses) reaches the sample 52, and nearly all the reflected probe beam 62 returns to the light source 40 to be amplified. This is because there is no optical splitting component such as a coupler between the light source 40 and the sample 52, as there are in the prior art devices mentioned. Due to this arrangement, the light source 40 can function simultaneously as a light source and amplifier to amplify the weak reflected probe beam 62. This boosts the strength of the reflected probe beam which leads to deeper scanning capability or faster scanning. Further, these benefits are provided without adding additional active components.

Figure 6:
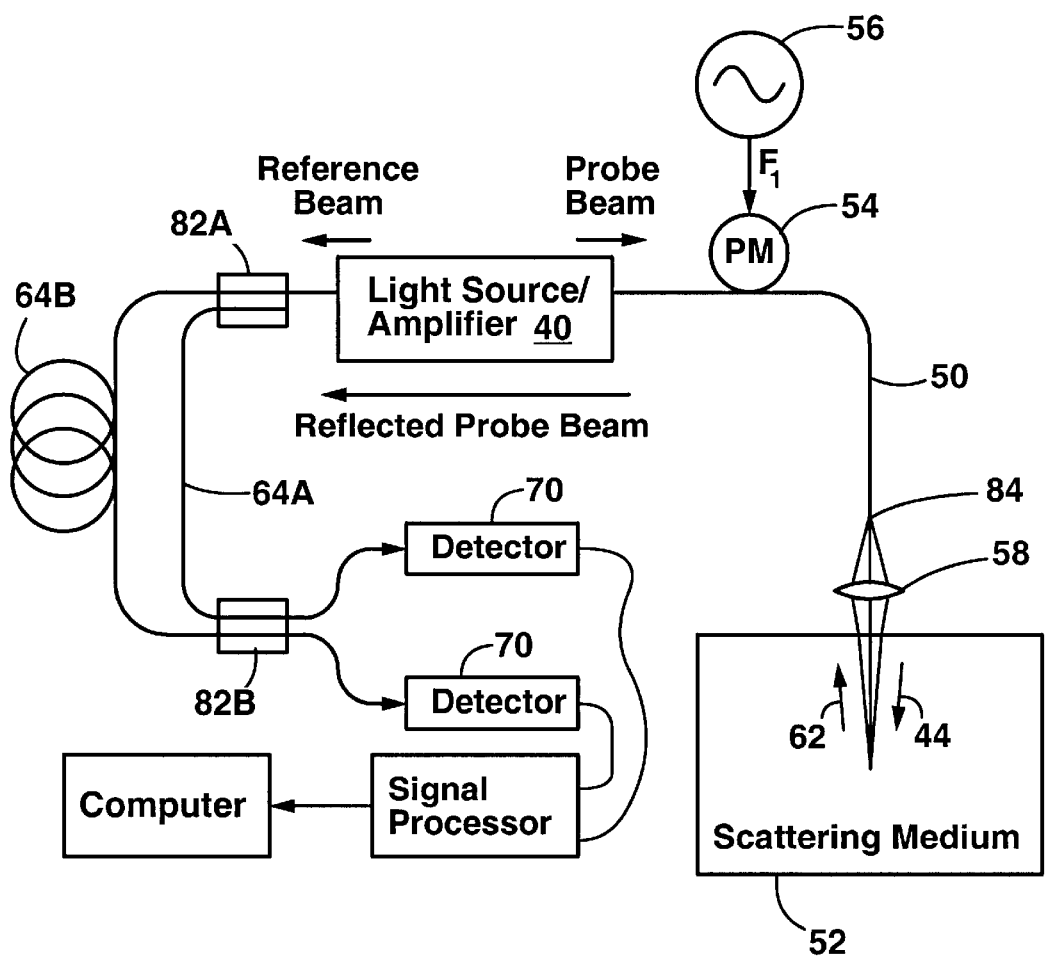
FIG. 6 is a reflectometer according to the present invention which uses fiber optic components.

FIG. 6 shows a second embodiment of the apparatus which differs from the first embodiment in that it uses optical fiber components. Optical fiber components are preferred for their low cost, ruggedness, flexibility, and resistance to misalignment. All of the optical fibers used in the embodiment of FIG. 6 are preferably single mode fibers. The light source is preferably an unpolarized light source. The light path 50 and the short arm 64A and long arm 64B comprise single mode optical fibers. 50/50 directional couplers 82A, 82B are substituted for the beamsplitters 65 of FIG. 2. The couplers 82A, 82B may be, for example, evanescent wave couplers or fused fiber couplers.

The probe beam 44 exits the light source 40 and propagates through an optical fiber to the sample. The phase modulator 54 in this embodiment can be a piezoelectric fiber stretcher. As the probe beam 44 exits the end of the optical fiber, it passes through the lens assembly 58 which focuses the probe beam 44. The end 84 of the optical fiber acts as an aperture which, in combination with the lens 58, forms a spatial filter/confocal microscope apparatus for the reflected probe beam 62. Therefore, when an optical fiber is used as the light path 50, a separate spatial filter setup (as shown in FIG. 5) is not necessary. The reflected probe beam 62 is amplified as it returns through light source 40 as in the embodiment of FIG. 2. The amplified reflected probe beam and reference beam emerge from the light source 40 and enter into the long arm 64B and short arm 64A. The outputs of the second coupler 82B feed into the two detectors 70. Of course, the phase modulator 54 can also be located in either arm 64A, 64B of the interferometer, as described above for the embodiment of FIG. 2.

FIGS. 7A, 7B, 7C, and 7D show examples of a few fiber-coupled two-port laser light sources which can provide the counterpropagating reference and probe beams 42, 44 used in the above embodiments of the present invention. The reference aperture 49 and the probe aperture 48 are shown for each light source. All the laser light sources have resonant cavities and provide higher power output than simple optical amplifiers.

Figure 7A:
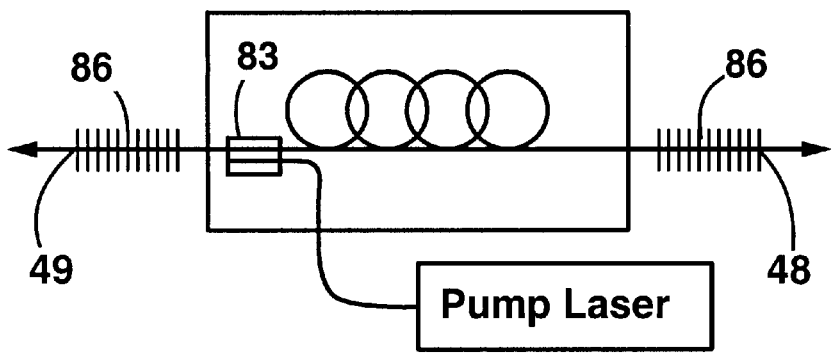
FIGS. 7A–7D show various examples of fiber-coupled two-output light sources which can be used in the reflectometer of FIG. 6.
Figure 7B:
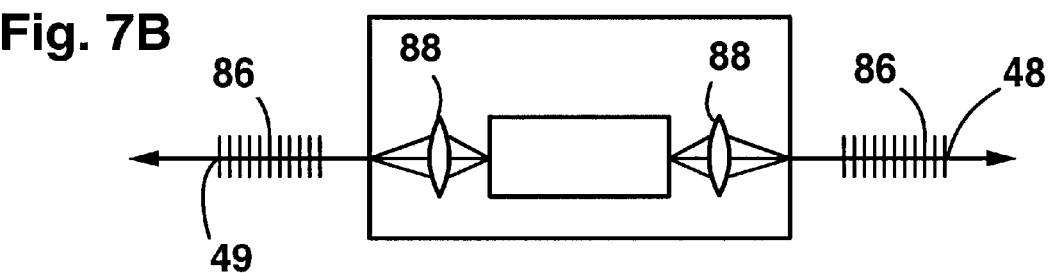
Figure 7C:
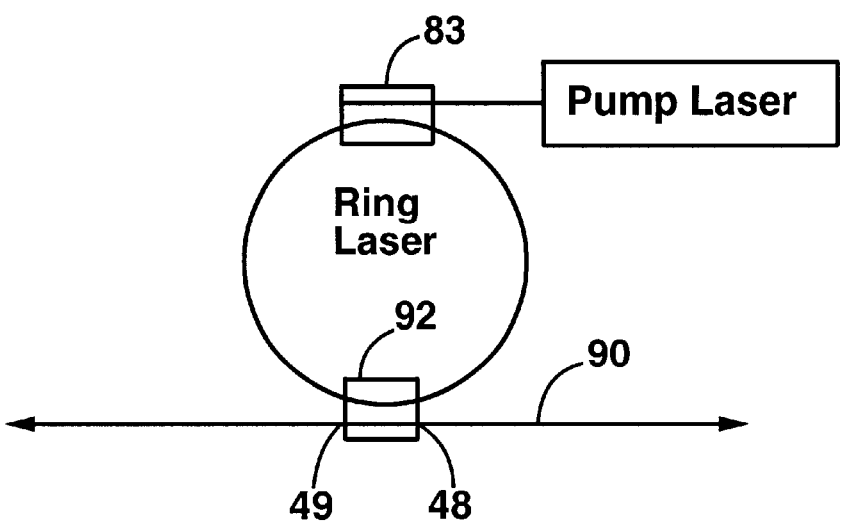
Figure 7D:
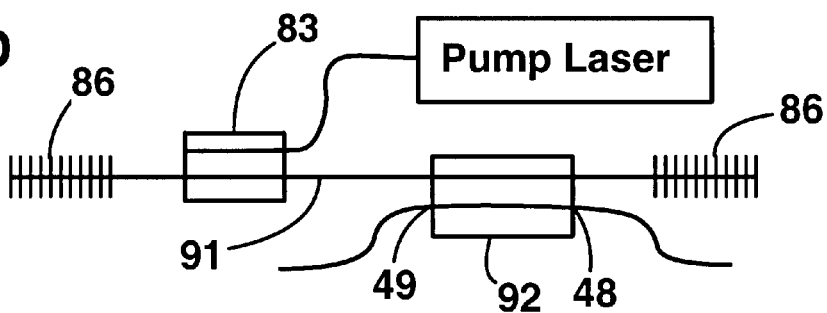

FIG. 7A shows a doped fiber laser which is pumped by a pump laser through a wavelength division multiplexer fiber coupler 83. The fiber laser may have broadband Bragg reflectors 86 on each side. FIG. 7B shows a two port fiber coupled semiconductor laser. Lenses 88 on each side of the laser couple the laser to optical fibers. The Bragg reflectors 86 of FIGS. 7A and 7B may be omitted to provide a weaker light source with shorter coherence length and which can provide amplification of the reflected probe beam. FIG. 7C shows a fiber ring laser coupled to a fiber 90 with a coupler and pumped with a pump laser through another coupler. The output coupler 92 in this embodiment may be a 90/10 or similar low coupling tap coupler. FIG. 7D shows another light source similar to FIG. 7C in which the ring laser is replaced with a linear fiber laser 91 having Bragg reflectors 86 on each end. In the embodiments of FIGS. 7C and 7D, the reference aperture 49 and probe aperture 48 are located on the output coupler 92.

Typically, short coherence length light sources have lower (diffraction limited) output power compared to long coherence length light sources. Therefore, a thin coherence gate interval will generally be associated with lower probe beam power. Depending on the scattering coefficient of the sample and the depth of imaging, a proper balance between the coherence gate interval and probe beam power can be found. In some cases if the tissue depth of interest is less than, for instance, 500 microns, a laser with a coherence length of 500 microns or more may be used, and increased sensitivity may be obtained by interfering the probe beam with the reference beam. In other cases, in order to eliminate glare, it may be necessary to work with a much shorter coherence length.

Figure 8A:
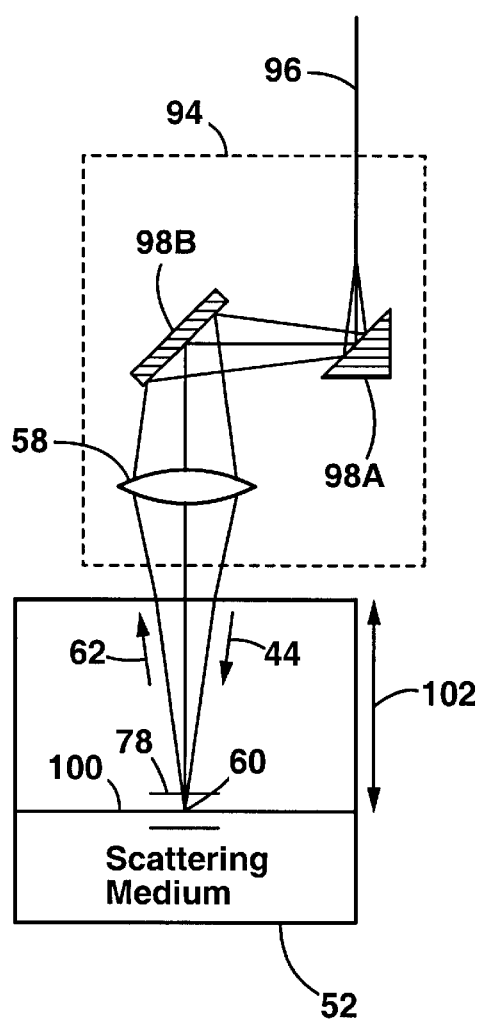
FIGS. 8A–8B show close-up views of transverse scanning heads used to provide imaging capability.

FIG. 8A shows a close-up of a scanning optical head which is preferably used in the present invention. The scanning head is used to produce reflectance images by moving the focal point 60 through the sample 52. The head is located at the sample end of the light path and so interfaces the probe beam 44 into the sample and collects the reflected probe beam 62. The head comprises all the components within the dotted area 94. The light path is an optical fiber 96. The optical fiber delivers the probe beam 44 to a pair of mirrors 98A, 98B and the lens assembly 58. The second mirror 98B is preferably a silicon micromachined scanning mirror and can be pivoted at high speed about 1 or 2 axes to provide a line-scan or two-dimensional scanning of a plane 100 at a predetermined depth 102 within the sample. The depth 102 of the plane 100 can be changed by moving the scanning head in a direction perpendicular to the surface of the sample 52. The coherence gate interval 78 remains in a fixed position about focal point 60 as the scanning head is moved towards or away from sample 52 and as mirror 98B pivots. In this way, images of human skin can be obtained which consist of vertical sections, much like the images that pathologists are already accustomed to viewing under a traditional microscope.

Figure 8B:
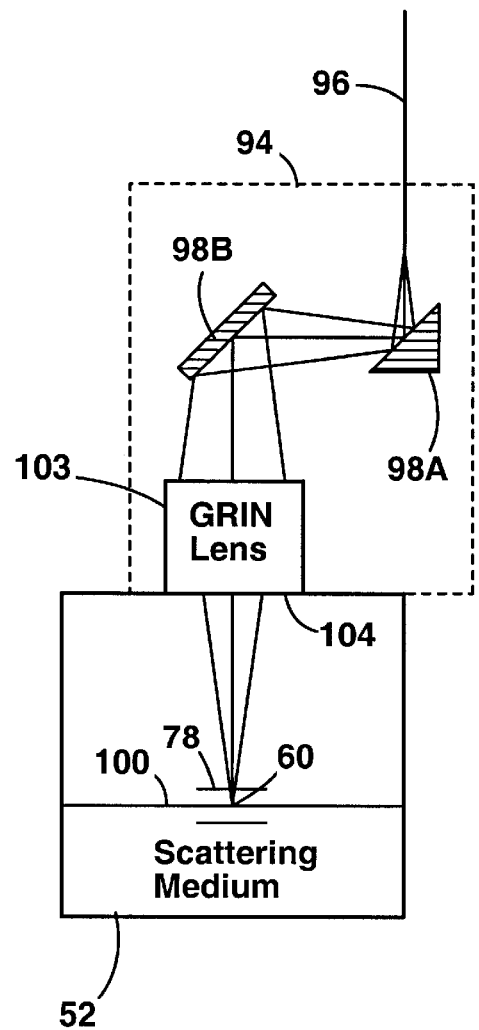

FIG. 8B shows the optical scanning head of FIG. 5A with a GRIN lens 103 which has a flat bottom 104. The flat bottom 104 allows close contact to be made between the lens 103 and the sample 52. An index matching fluid layer between the lens 103 and sample 52 can be used to minimize reflections. The total size of the scanning head shown in FIGS. 8A and 8B may be a millimeter or two on a side. The scanned area may be about 100 spot diameters across. For example, a device having a focused spot size of 5 $\mu$m may have a field of view of about 500 $\mu$m. A suitable micromachined mirror assembly is described in Optics Letters, "Micromachined Scanning Confocal Microscope", by D. L. Dickensheets and G. S. Kino, Vol. 21, No. 10, May 15, 1996, pp. 764–766. It will be apparent to one skilled in the art of optics that other scanning devices may be used.

Figure 8C:
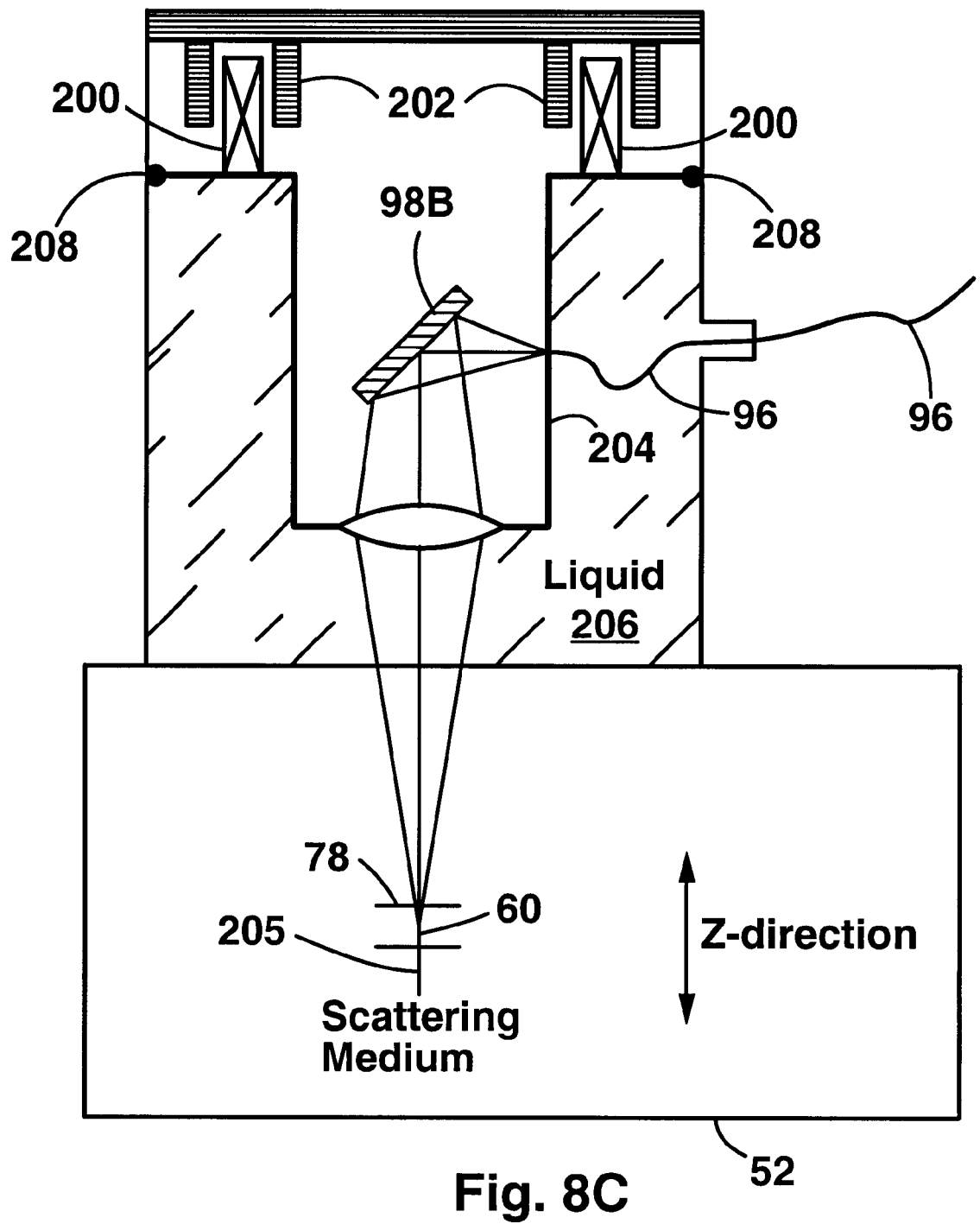
FIG. 8C shows an example of a vertical scanning head which can be used to scan in a direction parallel to a probe beam.

FIG. 8C shows an example of a scanning head capable of vertical section scanning. A voice coil motor comprising magnets 202 and voice coils 200 is used to move the focal point 60 in the Z-direction with respect to the sample 52. The voice coils 200 are attached to a movable carriage 204 and the magnets 202 are held fixed with respect to the sample 52. The lens assembly 58 and scanning mirror 98B are mounted to the carriage 204. As the voice coil is activated, the lens assembly, scanning mirror, and the focal point 60 are moved in the Z-direction. Thus, optical coherence is maintained between the reference beam and reflected probe beam for all positions of the focal point 60.

A region inside the carriage 204, between the lens assembly 58 and the sample 52, is filled with a liquid 206. The refractive index of the liquid 206 can be selected to match the refractive index of the sample 52, thereby minimizing reflections. The portion of the optical fiber 96 within the liquid 206 flexes as the carriage 204 moves so the optical path length to the focal point 60 is the same for all positions of the focal point 60. An O-ring seal 208 is provided to seal the liquid inside the carriage 204. Vertical scanning is performed at a slow frame rate of about 30 Hz while faster horizontal scanning at about 10 KHz is provided by the scanning mirror 98B. This produces an image of a vertical section 205 of the sample 52. Vertical section images can be used by those skilled in the art of performing biopsies. It will be apparent to one skilled in the art that other actuators may also be used to create scanned images.

For applications involving imaging through human skin, wavelengths in the range of 1.0 to 1.5 microns typically allow imaging to depths of no more than 3,000 microns. Therefore, a coherence gate interval thicker than 3,000 microns would not help reduce the unwanted backscattered light from the sample. Therefore, a light source having a coherence length greater than about 3000 microns would not be particularly useful. The depth of imaging should be considered when choosing a light source with a given coherence length. Also, it is noted that very short coherence lengths will require more accurate adjustment of the lengths of the interferometer arms 64A, 64B. Light sources with very short coherence lengths are typically much lower power and more expensive than long coherence length laser diodes.

Figure 9A:
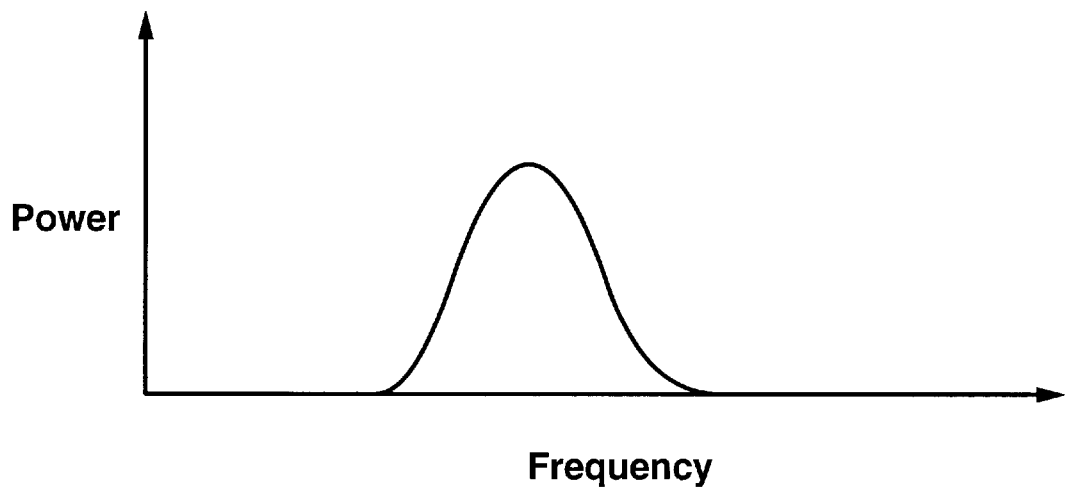
FIGS. 9A–9B show two frequency domain graphs illustrating the effect that a phase modulator has upon the spectrum of the probe beam.
Figure 9B:
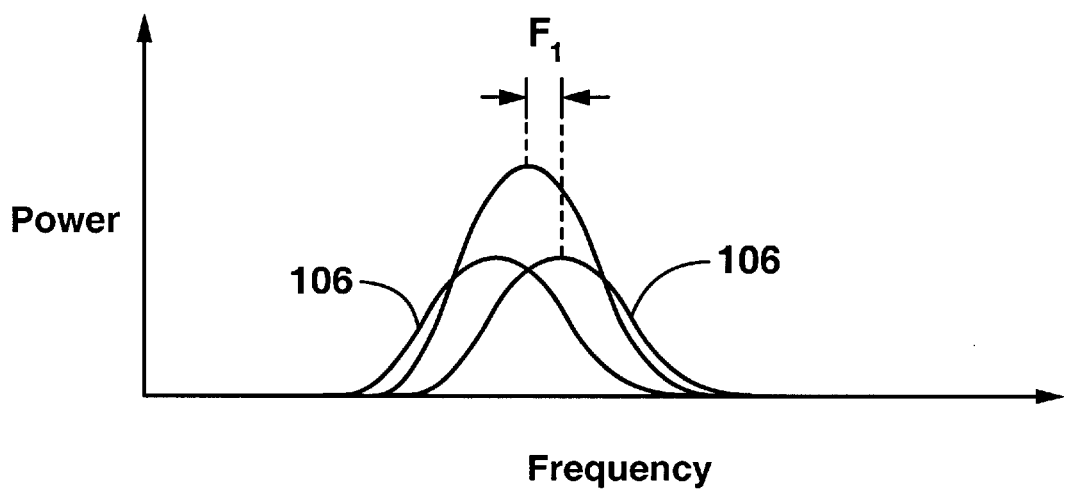

FIG. 9A shows the frequency spectrum of the original probe beam 44 and reference beam 42. FIG. 9B shows an example of the frequency spectrum of the probe beam 44 and reflected probe beam 62 after passing through the phase modulator 54. Driving the phase modulator sinusoidally at frequency $F_1$ produces two sidebands 106 on either side of the original probe beam 44 in the frequency spectrum. These sidebands are separated in frequency from the original probe beam 44 by frequency $F_1$. Therefore, when the (modulated) reflected probe beam is coherently recombined with the (unmodulated) reference beam, a beat frequency at frequency $F_1$ is created.

If scanning is being performed by the optical head (as shown in FIGS. 8A, 8B, and 8C) to create an image, then the beat frequency ($F_1$) should be selected with the scanning rate in mind. More specifically, the beat frequency should be substantially higher than the rate at which pixels inside the scattering sample medium are measured. This assures that the signal processor 72 is provided with several cycles over which it can measure the interference magnitude, and therefore the reflectance at the focal point 60 corresponding to the pixel. For example, if pixels are measured at a rate of 1 Mhz (fast enough for video), then the beat frequency (and the phase modulator driving frequency) should be at least about 10 Mhz. This will provide 10 interference fringes per pixel, which is sufficient to measure fairly accurately the reflectance of each pixel. The pixel scanning speed and the beat frequency may depend upon the particular application, of course. If high accuracy is required of the reflectance measurements, then frequency $F_1$ may be increased or the pixel scanning rate may be reduced.

For some applications, it may be desirable to have high phase modulation frequencies in the range of approximately 300–500 Mhz. This would be desirable, for example, for applications employing high scanning speeds with high spatial resolution and high reflectance accuracy. In these cases it may be necessary to abandon piezoelectric fiber stretcher phase modulators in favor of phase modulators based on electrooptic crystals such as lithium niobate. Electrooptic crystal phase modulators are generally capable of much higher modulation frequencies.

An alternative is to use an acousto-optic modulator. This device has the advantage that it gives single sideband modulation which makes the problem of demodulation of the output signal as a function of the focal point location a little simpler if a narrow band laser is used as the source. With a narrow band, long coherence length laser, the output signal from the detectors will vary rapidly in sinusoidal fashion with focal point location. Since only the envelope of this signal is needed, the envelope must be extracted from this signal by using processes well known to those skilled in the art. However, with single sideband modulation, the envelope required is obtained as the direct output from the detectors. It will be apparent to one skilled in the art of phase modulator design how to select a specific phase modulator for a given apparatus and application.

It is noted that the phase modulator can be driven by waveforms other than sinewaves. A triangular waveform, for example, creates a more complicated pattern of sidebands in the frequency spectrum of the probe beam. These sidebands cause interference in the same manner as a sinusoidal driving function, although the resultant heterodyne interference beats picked up at the detector 70 will be more complicated. Also, the phase modulator 54 can be operated in a constant displacement mode. For example, a ramp waveform applied to the phase modulator results in a constant Doppler shift in the frequency of the probe beam during the sloping part of the ramp waveform. Data can be collected during the sloping part of the ramp and the resultant beat frequency will be equal to the Doppler shift of the probe beam 44. It will be apparent to one skilled in the art of heterodyne interferometry techniques that there exist many ways of modulating or shifting the frequency of the probe beam (or reference beam 42 or reflected probe beam 62) such that a detectable beat frequency is generated at the detectors 70.

The aforementioned embodiments of the present invention inherently lose 50% of each of the reference beam 42 and reflected probe beam 62. In other words, 50% of each beam (reference beam and reflected probe beam) does not contribute to the coherent interference at the detectors 70. More specifically, the portion of the reference beam 42 which travels down the short arm 64A of the interferometer does not contribute to the interference detected by the detectors because it is incoherent with respect to the reflected probe beam 62. Similarly, the portion of the reflected probe beam 62 which travels down the long arm 64B of the interferometer does not contribute to interference because it is incoherent with respect to the reference beam. While the first and second embodiments are an improvement over the prior art, still further improvements in light usage efficiency can be achieved. This problem is addressed in the following embodiments of the present invention.

Figure 10:
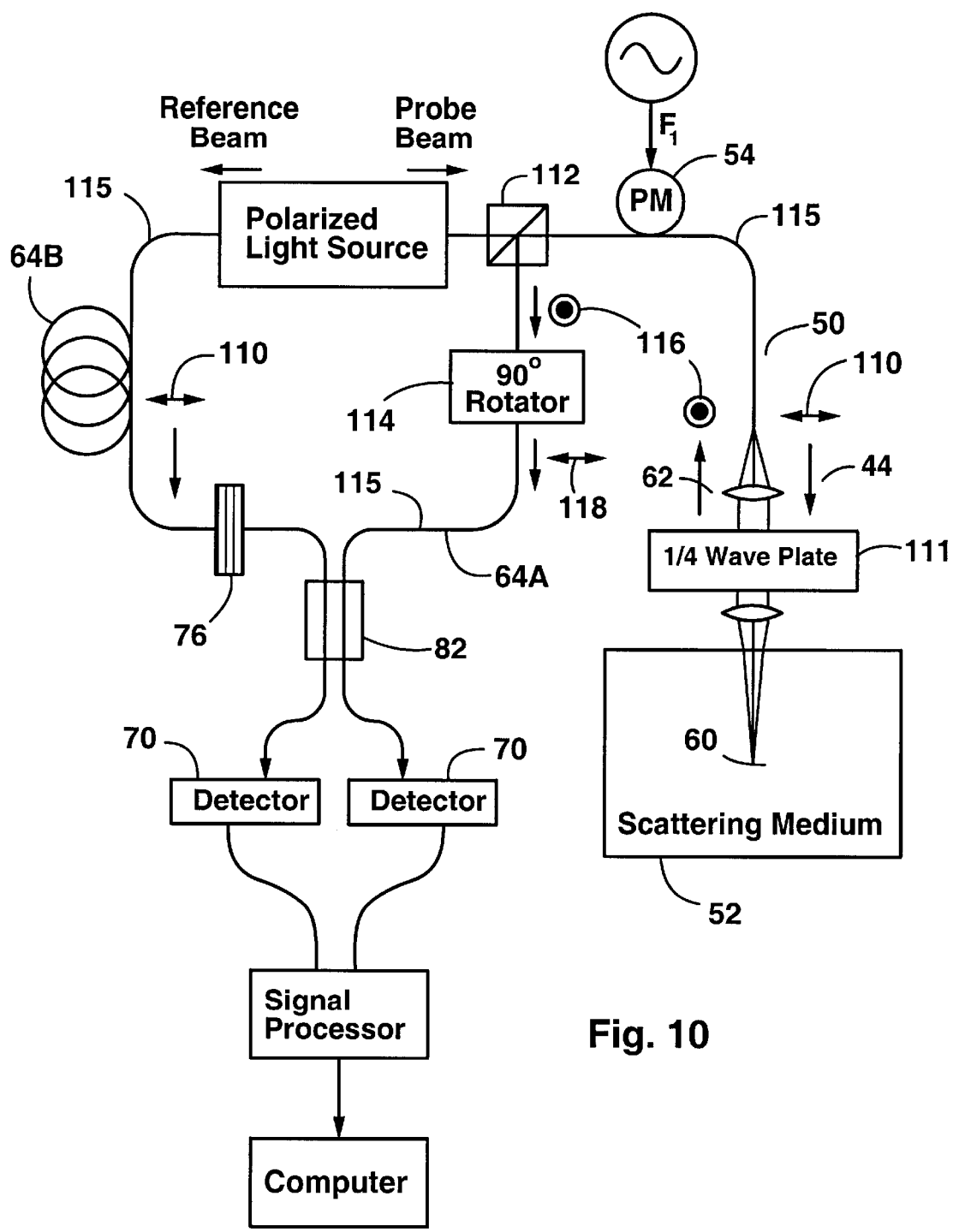
FIG. 10 shows a reflectometer according to the present invention which uses polarized light.

The embodiment of FIG. 10 causes nearly 100% of both the reference beam and reflected probe beam to contribute to the temporal interference at the detector 70. This is quite beneficial because it greatly increases the signal to noise ratio, which in turn makes higher contrast and deeper images possible.

The embodiment of FIG. 10 uses polarized light techniques to independently control the reference and reflected probe beams and thereby cause 100% of the reflected probe beam to contribute to the temporal interference. This embodiment preferably uses polarization preserving optical fiber, but bulk optical components may also be used.

The embodiment of FIG. 10 has a fiber coupled polarizing beamsplitter 112, and a 90° double pass polarization rotation element 111 located in the light path. The polarization rotation element can be a ¼ wave plate or faraday rotator. The light path is made of a polarization maintaining fiber 115 which is capable of supporting two orthogonal polarizations. The short arm 64A has a single pass polarization rotator 114 such as a ½ wave plate, optically active chiral material, 90° fiber twist, or faraday rotator. Preferably, both arms 64A, 64B are comprised of lengths of polarization maintaining optical fiber 115.

A polarized light source emits counterpropagating reference and probe beams which have the same polarization. Both reference and probe beams have a "lateral" polarization which is represented by arrows 110. The double pass 90° polarization rotation element 111 is located between the light source and sample 52 so that the reflected probe beam has a polarization orthogonal to the probe beam and reference beam. Concentric circles 116 represent the polarization of the reflected probe beam.

The reflected probe beam 62 is reflected out of the light path and into the short arm 64A by the polarizing beamsplitter 112. The reflected probe beam then passes through the single pass 90° polarization rotator 114 and emerges with a polarization 118 parallel with the reference beam. Meanwhile, the reference beam propagates through a predetermined length of polarization maintaining fiber 115 which comprises the long arm 64B of the interferometer. The reference beam and reflected probe beam are then combined at a directional coupler 82 such that coherent interference is produced.

The coupler 82 may be a polarization maintaining evanescent wave coupler or fused fiber coupler, for example. The temporal interference caused by the phase modulator 54 is thus detected and measured and all the light from the reflected probe beam contributes to the interference. An adjustable attenuator 76 can also be used to attenuate the reference beam such that maximum signal-to-noise ratio is provided at the detector 70. Alternatively, a balanced detection scheme may be used to subtract one component of noise riding on the reference beam. The single pass 90° polarization rotator 114 which effects the reflected probe beam can alternatively be located in the path (long arm 64B) of the reference beam.

As in the previously described embodiments, the optical path length which the reference beam travels is selected to match the total path length traversed by the reflected probe beam such that coherent interference occurs at the coupler 82 and detectors 70. Also, a variable optical delay device can be included anywhere in the system between coupler 82 and sample 52 so that small path length adjustments can be made to maintain coherence between the reference beam and reflected probe beam. Adjusting the relative path length allows the coherence gate interval to be moved longitudinally to the desired fixed position about the focal point 60.

An optical amplifier such as a two-port fiber amplifier may be included to amplify the reflected probe beam 62. Such an amplifier may be placed anywhere between the polarizing beamsplitter 112 and coupler 82. The signal strength of the reflected probe beam is increased if the reflected probe beam is amplified, allowing faster scanning rates because a shorter measurement time is then required for each pixel.

The embodiment of FIG. 10 uses the reflected probe beam much more efficiently than prior art devices because all of the reflected probe beam contributes to the interference. The signal amplitude is maximized for a given intensity of the reflected probe beam, and an improved signal-to-noise ratio results.

The phase modulator 54 can be placed in locations other than the location shown. For example, it can be placed in the reference beam path (i.e. in the interferometer long arm 64B) so that it modulates only the reference beam. Alternatively, the phase modulator 54 can be placed between the polarizing beamsplitter 112 and coupler 82 so that it modulates only the reflected probe beam.

Placing the phase modulator 54 in one of the interferometer arms 64A, 64B may improve the operation of the device because light will only pass through the phase modulator once. By comparison, if the phase modulator is located in the light path 50, then the reflected probe beam will have passed through the phase modulator twice upon its arrival at detector 70. Having the modulated light make only a single pass through the modulator 54 is desirable because it avoids possible multiple phase modulation problems which may arise from the time delay between first and second passes through the modulator. Single pass modulation, therefore, can increase the maximum possible modulation frequency, thereby improving the resolution of the reflectometer. Such issues will be apparent to one skilled in the art of heterodyne interferometry.

Some kinds of phase modulators ($LiNbO_3$ waveguide modulators, for example) are only transparent to light having a specific polarization. A modulator of this type cannot be placed in the light path 50, because the light path must be transparent to two orthogonal polarizations. Therefore, a modulator of this type must be placed within one of the interferometer arms 64A, 64B.

Figure 11:
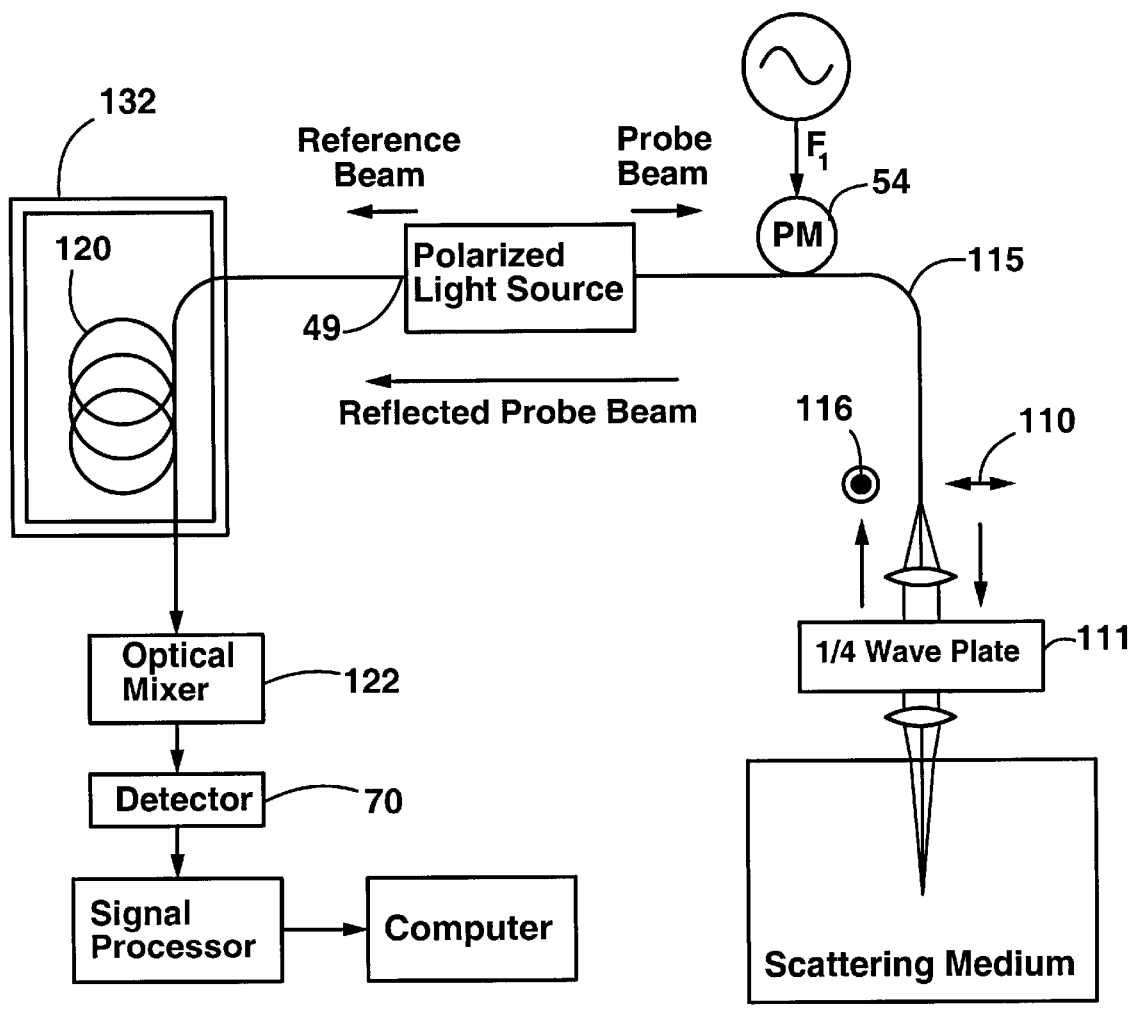
FIG. 11 shows a reflectometer according to the present invention which uses polarized light and a birefringent fiber.

An alternative embodiment which uses polarized light is shown in FIG. 11. As in the embodiment of FIG. 10, 100% of the reflected probe beam contributes to the interference, i.e. none of the reflected probe beam is wasted. Here, the interferometer is made of a single length of birefringent optical fiber 120. The birefringent fiber performs the function of both arms 64A, 64B. No beamsplitters are used, although the 90° double pass polarization rotation element 111 is used in the light path. The light source of FIG. 11 should be polarized but also transparent to an orthogonal polarization. The polarized light source may be a laser with a Brewster window, for example.

The polarization of the reflected probe beam is rotated by 90° with respect to the original probe beam by the polarization rotation element 111. Arrow 110 and concentric circle 116 represent the polarizations of the probe beam and reflected probe beam, respectively. The reflected probe beam then passes through the polarized light source. Of course, the polarizing element of the light source must not block the reflected probe beam. The reflected probe beam then emerges from the reference aperture 49 combined with the reference beam.

The combined beams are then passed to the length of birefringent optical fiber 120. The birefringent fiber 120 is oriented such that the reference beam is affected by a higher index of refraction than the reflected probe beam. Therefore, the birefringent fiber 120 provides both arms 64A, 64B of the interferometer. The length of the birefringent fiber can be selected such that the reference and reflected probe beams emerge with coherence restored. The beams still have orthogonal polarizations when they exit the fiber, so an optical mixer 122 is required to align (homogenize) the orthogonal polarizations to obtain interference.

Figure 12:
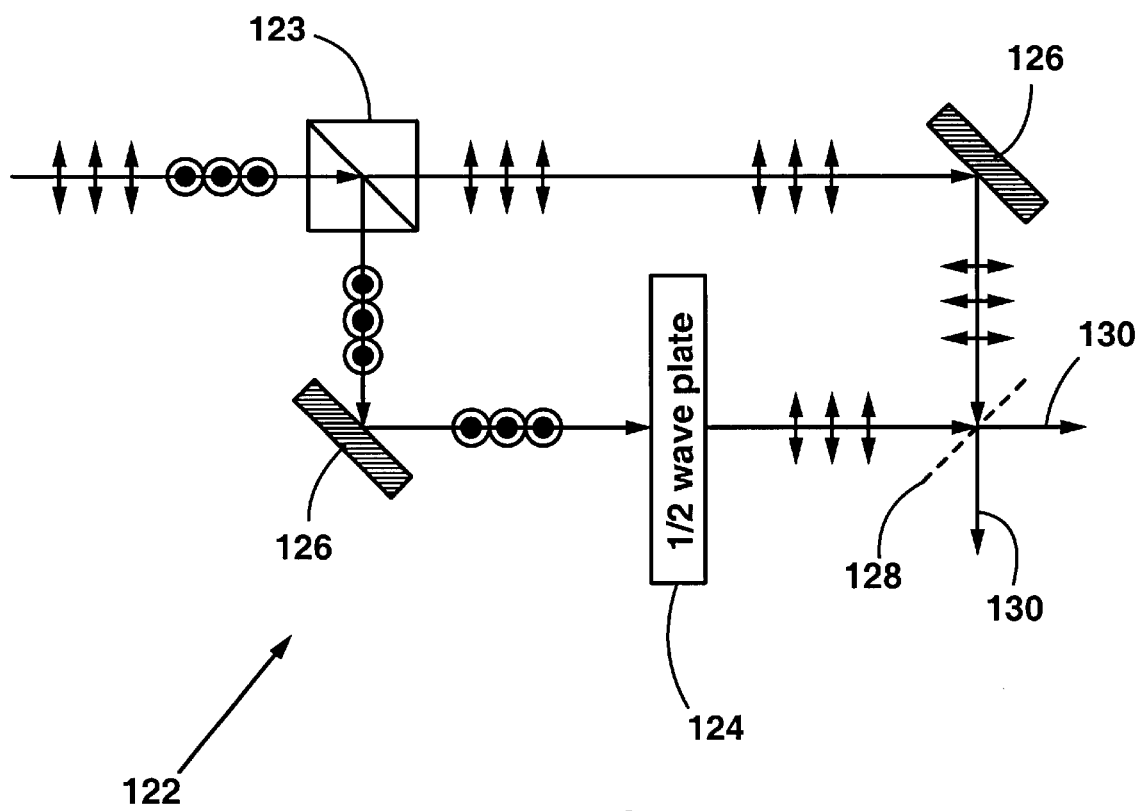
FIG. 12 shows an optical mixer which can be used in an interferometer to coherently combine two beams with orthogonal polarizations.

An example of an optical mixer 122 which can be used in the apparatus of FIG. 11 is shown in FIG. 12. A polarizing beam splitter 123 separates the beams by polarization and one beam passes through a ½ wave plate 124 or other 90° polarization rotator. Mirrors 126 direct the two beams to a beam splitter 128 where they are combined. The two exiting beams 130 then pass into two detectors. It will be apparent to one skilled in the art of optics that other optical mixers 122 can be designed which will work in the present invention. For example, fiber components such as polarizing beamsplitters and polarization maintaining evanescent wave couplers can be used to make fiber-based optical mixers.

It is noted that some kinds of birefringent optical fiber have a non-zero temperature coefficient of birefringence. Therefore, in the embodiment of FIG. 11 the optical path difference for the reference and reflected probe beams 120 can be controlled by adjusting the temperature of the fiber. The birefringent fiber 120 of FIG. 11 can be placed in a temperature controlled oven 132 to control the path length difference. As a specific example, a 100 meter length coil of high birefringence optical fiber can give an optical path displacement of about 10 microns per ° C. This embodiment provides a method of controlling the optical path length and location of the coherence gate interval without moving parts.

Alternatively, control of the optical path length difference between the two orthogonal polarization modes in the birefringent fiber 120 can be accomplished by winding the birefringent fiber around a piezoelectric drum fiber stretcher. This allows fast adjustment of the position of the coherence gate interval 78 relative to the focal point 60, as shown in FIG. 3.

Figure 13:
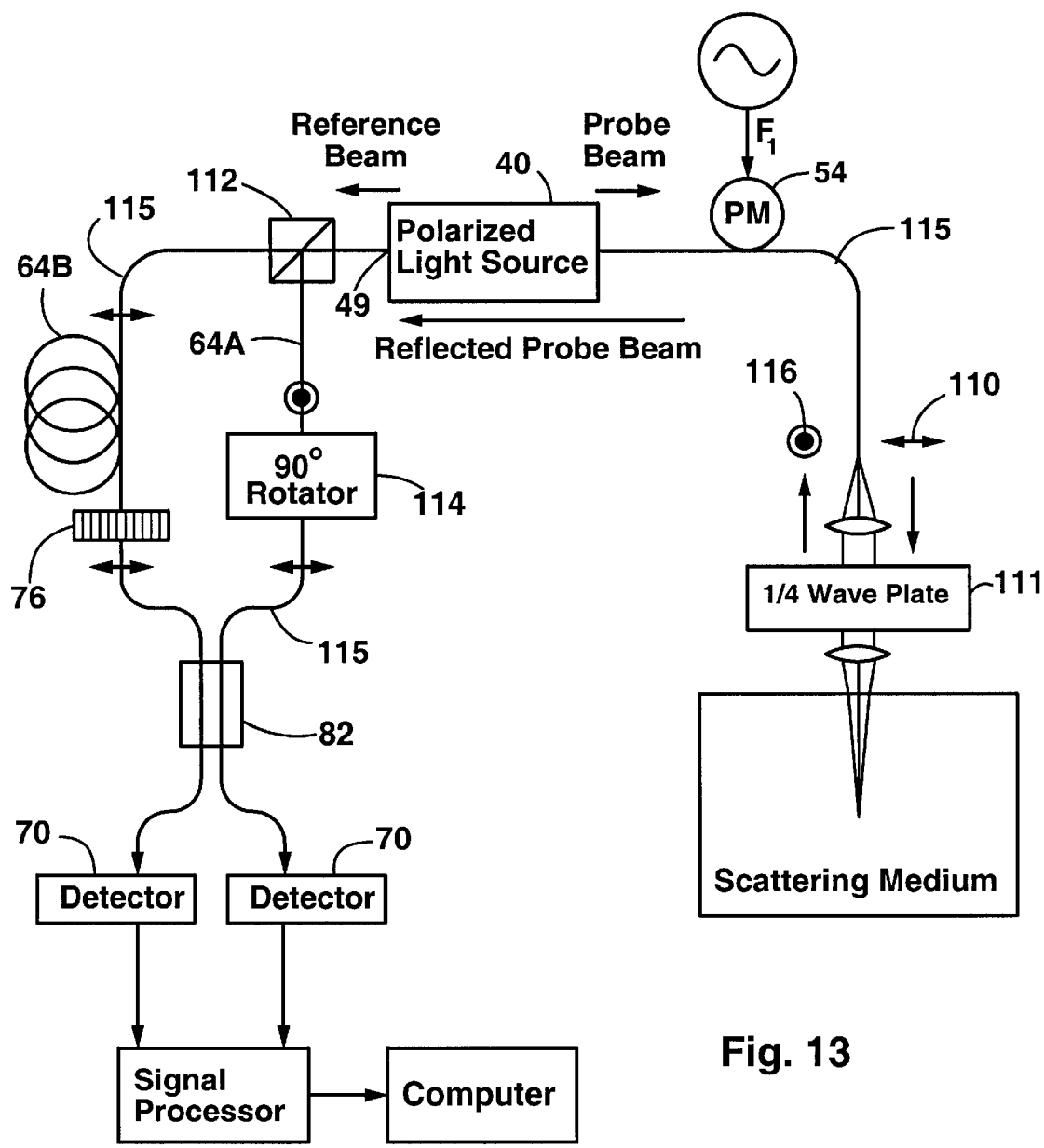
FIG. 13 shows a reflectometer according to another embodiment of the present invention which uses polarized light.

FIG. 13 shows an apparatus according to another embodiment of the present invention which exploits polarized light. This embodiment has a fiber coupled polarizing beamsplitter 112 located between the reference aperture 49 and the interferometer. Polarization maintaining optical fiber 115 is used throughout the apparatus. The reflected probe beam passes through the light source 40 and emerges from the reference aperture 49 combined with the reference beam. The polarizing beamsplitter 112 then separates the reflected probe beam and reference beam such that the reflected probe beam is sent through the short arm 64A and the reference beam is sent through the long arm 64B.

The short arm 64A includes a 90° single pass polarization rotator 114. The long arm 64B may include the adjustable attenuator 76, as shown. Alternatively, the attenuator may not be used and the method of balanced detection employed. The coupler 82 is used to recombine the reference beam and reflected probe beam before they enter the detectors. The coupler 82 should be a polarization maintaining coupler. The 90° rotator 114 can alternatively be located in the long arm 64B.

Figure 14:
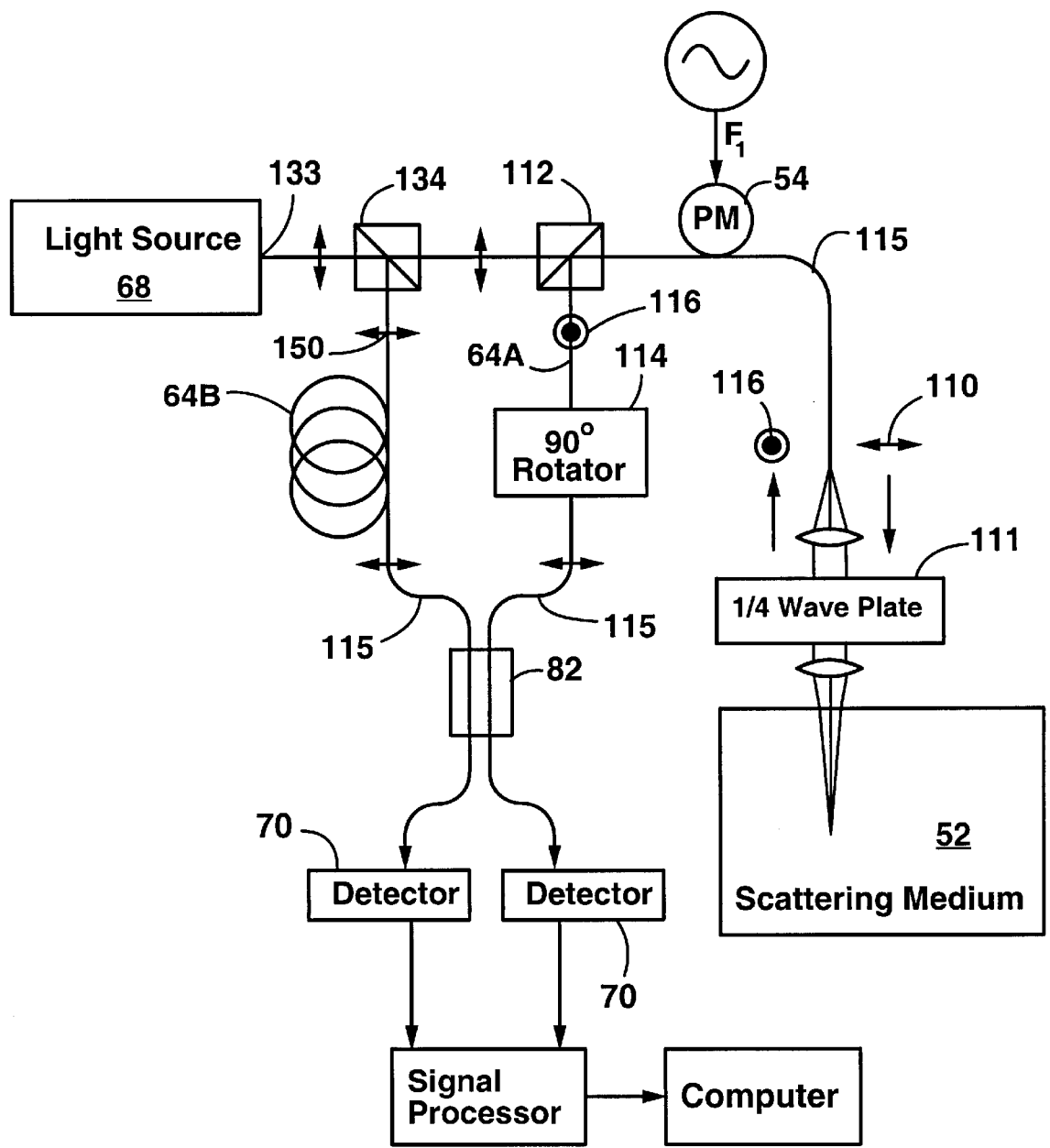
FIG. 14 shows a reflectometer according to an alternative embodiment of the present invention which uses a single output light source.

FIG. 14 shows an embodiment of the present invention in which both the reference beam and the probe beam are emitted from a single light source aperture 133. The single output light source 68 of this embodiment is polarized and polarization maintaining fiber 115 provides the light path and the arms 64A, 643 of the interferometer. A first beamsplitter 134 (nonpolarizing) is used to create the reference beam from the probe beam emitted from the single aperture 133. The splitting ratio of the first beamsplitter 134 in this embodiment can be used to control the power of the reference beam 42 such that the signal-to-noise ratio is maximized. This may allow signal-to-noise improvement without the use of the separate attenuator 76 used in the previous embodiments. A second polarizing beamsplitter 112 is located in the light path between the source and sample.

The nonpolarizing first beamsplitter 134 is oriented such that the reference beam is routed into the long arm 64B. The polarization of the reference beam is indicated by an arrow 150. The probe beam continues through the first beamsplitter 134 to the sample 52. The reflected probe beam returns from the sample and has a polarization orthogonal to the probe beam and reference beam due to the 90° double pass polarization rotation element 111. The polarizations of the probe beam and the reflected probe beam are indicated by the arrow 110 and circle 116, respectively.

The reflected probe beam is routed into the short arm 64A by the second polarizing beamsplitter 112. The second polarizing beamsplitter 112 reflects only the reflected probe beam and not the original probe beam because the reflected probe beam has a polarization orthogonal to the original probe beam. The polarization rotator 114 is located in the short arm to align the polarization of the reflected probe beam parallel with the polarization of the reference beam. The reflected probe beam and reference beam are then combined at a coupler 82 and the resulting interference is detected at the detectors 70. In the embodiment of FIG. 14, all of the reflected probe beam contributes to the interference.

A variable optical delay should be included in the long or short arm of the interferometer to provide control over the location of the coherence gate interval 78 with respect to the focal point 60, as shown in FIG. 3. Additionally, an amplifier (such as an optical fiber amplifier) may be included in the short arm 64A to amplify the reflected probe beam and to increase the signal strength of the reflected probe beam. The single pass polarization rotator 114 can be alternatively located in the long arm 64B. In addition, the phase modulator 54 can be alternatively located in the short arm 64A or the long arm 64B.

Figure 15:
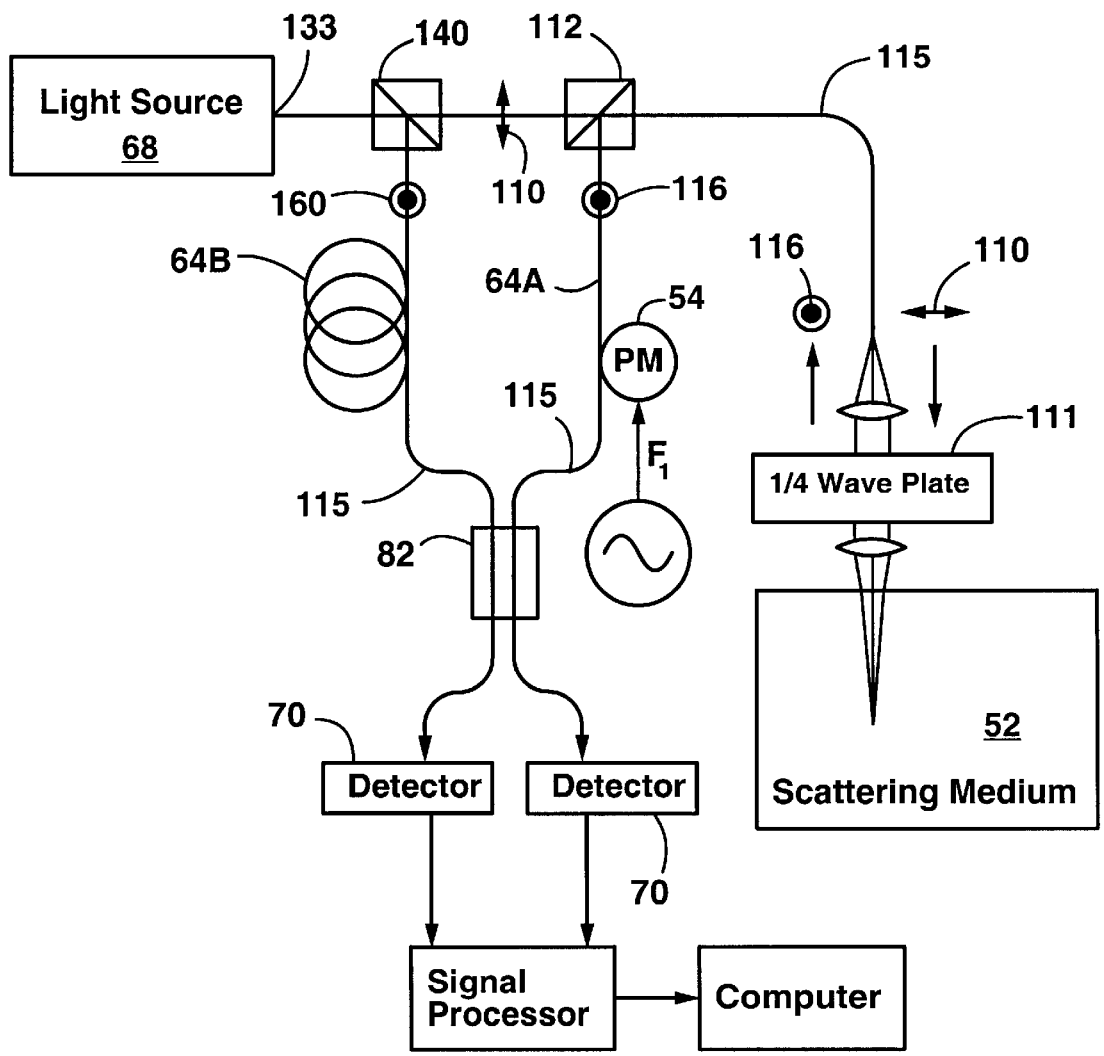
FIG. 15 shows a reflectometer according to another embodiment of the present invention.

FIG. 15 shows an apparatus for performing optical coherence domain reflectometry according to another embodiment of the invention. A first polarizing beamsplitter 140 is located in the light path between the single output light source 68 and the sample 52. The second polarizing beamsplitter 112 is also located in the light path. The light source in the embodiment of FIG. 15 may or may not be polarized.

Polarization maintaining optical fiber 115 is preferably used throughout the system. Light emitted from the single aperture 133 is incident upon the first polarizing beamsplitter 140, creating the reference beam which is routed into the long arm 64B. The probe beam continues through the first polarizing beamsplitter 140. The reference beam and the probe beam thus have orthogonal polarizations. Circles 160 represent the polarization of the reference beam and arrows 110 represent the polarization of the probe beam. Circles 160 and arrows 110 indicate orthogonal polarizations. The reflected probe beam has a polarization parallel with the reference beam due to the double pass polarization rotation element 111. Circles 116 indicates the polarization of the reflected probe beam. The second polarizing beamsplitter 112 is oriented such that the reflected probe beam is routed into the short arm 64A.

The reflectometer of FIG. 15 does not require the polarization rotator 114 of FIG. 14. This is an advantage over the embodiment of FIG. 14 because it reduces the cost of the device and the number of components. Another advantage of the reflectometer of FIG. 15 is that, in the case of a polarized light source, the orientation of the first beamsplitter 140 determines the amount of optical power which is in the reference beam. This allows for continuous adjustment of the reference beam power without the need for an optical attenuator in the long arm 64B.

FIG. 15 shows the phase modulator 54 located in the short arm 64A, which results in a single pass of the reflected probe beam through the modulator 54. Alternatively, the phase modulator can be located in the long arm 64B, or anywhere in the light path. Also, a variable optical path length delay device may be located in one of the arms 64A, 64B or in the light path for adjusting the location of the coherence gate interval with respect to the focal point. An amplifier (fiber or semiconductor) can be placed in arm 64A to boost the strength of the reflected probe beam.

Figure 16:
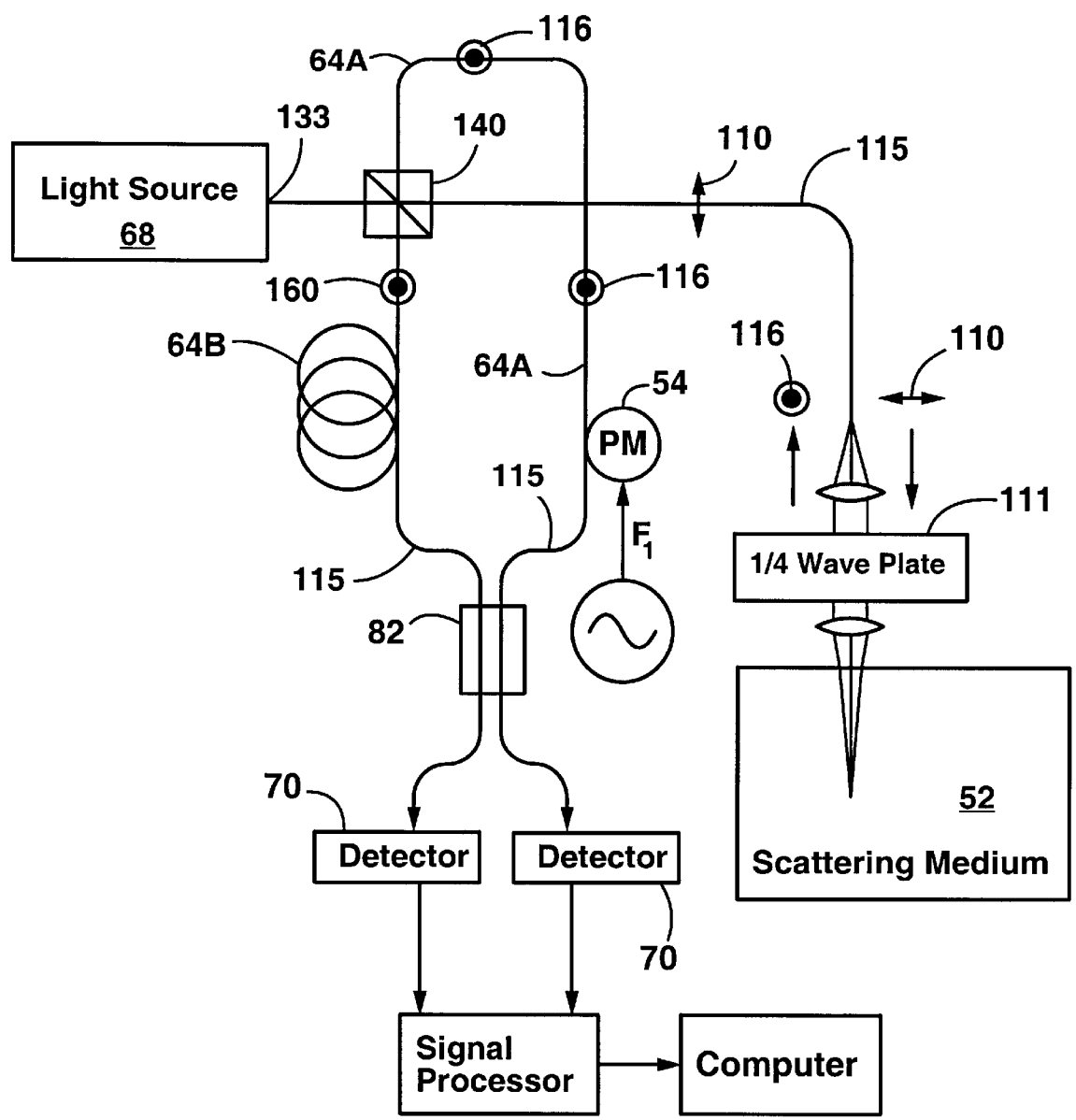
FIG. 16 shows a reflectometer according to a preferred embodiment of the present invention.

FIG. 16 shows an apparatus according to the preferred embodiment of the present invention. The apparatus includes a single polarizing beamsplitter 140 which is located in the light path between the light source 68 and the sample 52. The light source 68 may be polarized or nonpolarized. Polarization maintaining optical fiber 115 is preferably used throughout the apparatus. Light emitted by the single aperture 133 is incident upon the polarizing beamsplitter 140, creating the reference beam and the probe beam.

The reference beam is directed by the beamsplitter 140 into the long arm 64B and has a polarization represented by the circles 160. The probe beam has a polarization represented by the arrows 110. The reflected probe beam has a polarization parallel with the reference beam due to the double pass polarization rotation element 111. The reflected probe beam has a polarization represented by the circles 116. The reflected probe beam is directed into the short arm 64A by the polarizing beamsplitter 140. The reference beam and reflected probe beam, having parallel polarizations, are combined at the coupler 82.

There are many types of fiber couplers that may be used in the embodiments of FIGS. 6, 10, 11, 13, 14, 15, and 16. For example, the function of first nonpolarizing beamsplitter 134 can be realized using a polarization maintaining variable ratio evanescent wave coupler. The function of polarizing beamsplitter 112 can be realized using a polarizing beamsplitter evanescent wave coupler, and coupler 82 can be realized using a polarization maintaining 50/50 fixed ratio evanescent wave coupler. The use of these fiber couplers is well known in the art of fiber-optic gyroscopes and fiber interferometers.

The scanning heads of FIGS. 8A, 8B, or 8C can be combined with the embodiments of FIGS. 2, 6, 10, 11, 13, 14, 15, or 16 to allow for imaging. It will be apparent to one skilled in the art of constructing optical systems how to combine these elements.

The present invention provides a reflectometer which can produce real-time video images of the internal structure of turbid materials. Thus, the present invention can be used to provide images of biological tissues. For example, the reflectometer of the present invention can be used to image through skin or within arteries or vessels to analyze the arterial walls. For imaging through biological tissue or human skin, certain spectral regions are known which have low absorption and scattering coefficients and therefore allow deeper imaging or better image contrast. For example, it is well known that human skin is particularly transparent in the wavelength range of 0.8 to 1.6 microns. Therefore, a light source which produces light in this range should be used in the apparatus of the present invention when attempting to image through human skin. It will be apparent to one skilled in the art of imaging that such considerations are important in choosing the light source and wavelength range for a particular application.

The invention can be made using a small number of fiber components for reliability, low cost, flexibility, and ease of assembly.

It will be clear to one skilled in the art that the above embodiments may be altered in many ways without departing from the scope of the invention. Accordingly, the scope of the invention should be determined by the following claims and their legal equivalents.

What is claimed is:

1. An apparatus for performing optical coherence domain reflectometry on a sample, the apparatus comprising:
   a) a two output polarized light source having:
      i) a probe aperture for emitting a probe beam; and
      ii) a reference aperture for emitting a reference beam; wherein the light source is located such that a light path exists between the probe aperture and the sample.
   b) a 90° double pass polarization rotation element located in the light path such that a reflected beam reflected from the sample is orthogonally polarized with respect to the probe beam;
   c) an interferometer having a short arm and a long arm, wherein the long arm is positioned to receive the reference beam;
   d) a polarizing beamsplitter located in the light path for diverting the reflected beam into the short arm, wherein the long arm and the short arm have an optical path length difference selected to provide optical coherence between the reference beam and the reflected beam; and
   e) a polarization rotator located in the interferometer such that the reference beam and the reflected beam have substantially the same polarization at the output of the interferometer.

2. The apparatus of claim 1 further comprising a transverse scanning mechanism in the light path for producing reflectance images.

3. The apparatus of claim 2 wherein the scanning mechanism comprises at least one scanning mirror.

4. The apparatus of claim 3 wherein the scanning mirror is a micromachined scanning mirror.

5. The apparatus of claim 3 wherein the scanning mirror scans about one axis.

6. The apparatus of claim 3 wherein the scanning mirror scans about two axes.

7. The apparatus of claim 1 further comprising a vertical scanning mechanism in the light path for scanning in a direction parallel with the probe beam.

8. The apparatus of claim 1 wherein the light path further comprises a spatial filter for providing spatial filtering of the reflected beam.

9. The apparatus of claim 1 wherein the light path comprises a lens assembly for focusing the probe beam to a point within the sample, the lens assembly having a numerical aperture in the range of 0.4 to 1.4.

10. The apparatus of claim 1 wherein the interferometer comprises two polarization maintaining optical fibers of unequal length.

11. The apparatus of claim 1 wherein the light path comprises a polarization maintaining optical fiber capable of supporting two independent orthogonal polarization modes.

12. The apparatus of claim 1 further comprising a phase modulator for modulating the phase of either the reference beam or the reflected beam.

13. The apparatus of claim 12 wherein the phase modulator is located within the light path.

14. The apparatus of claim 12 wherein the phase modulator is located within one arm of the interferometer.

15. The apparatus of claim 12 wherein the phase modulator is a piezoelectric fiber stretcher, an electrooptic crystal, or an acousto-optic modulator.

16. The apparatus of claim 1 further comprising a frequency shifting means for shifting the frequency of either the reference beam or the reflected beam.

17. The apparatus of claim 16 wherein the frequency shifting means is located within the light path.

18. The apparatus of claim 16 wherein the frequency shifting means is located within one arm of the interferometer.

19. The apparatus of claim 1 wherein the polarizing beamsplitter is a polarizing beamsplitter evanescent wave optical fiber coupler.

20. The apparatus of claim 1 wherein the double pass 90° polarization rotation element comprises a Faraday rotator.

21. The apparatus of claim 1 further comprising a variable optical delay device in at least one arm of the interferometer.

22. The apparatus of claim 1 further comprising a variable optical delay device disposed in the light path.

23. The apparatus of claim 1 wherein the coherence length of the light source is less than 3000 microns.

24. The apparatus of claim 1 wherein the short arm comprises an optical amplifier for amplifying the reflected beam.

25. The apparatus of claim 1 wherein the light source is of the type which produces light in the wavelength range of 0.8 to 1.6 microns.

26. The apparatus of claim 1 further comprising an optical detector.

27. A method for performing optical coherence domain reflectometry on a sample, the method comprising the steps of:
   a) producing a reference beam and a probe beam from a dual output polarized light source having a reference aperture and a probe aperture, wherein the reference beam and the probe beam are counterpropagating, and wherein the reference beam emerges from the reference aperture and the probe beam emerges from the probe aperture;
   b) passing the probe beam into the sample through a polarizing beamsplitter, wherein a portion of the probe beam is reflected by the sample to form a reflected beam;

c) rotating the polarization of the reflected beam compared to the probe beam such that the reflected beam and the probe beam have orthogonal polarizations.
d) routing the reflected beam into a short arm of an interferometer using the polarizing beamsplitter;
e) sending the reference beam to a long arm of the interferometer;
f) rotating the polarization of either the reflected beam or the reference beam such that the reflected beam and the reference beam have substantially the same polarization; and
g) combining the reference beam and the reflected beam such that coherent interference is produced.

28. The method of claim 27 further comprising the step of modulating the phase of either the reference beam or the reflected beam to modulate the coherent interference.

29. The method of claim 27 further comprising the step of shifting the frequency of either the reference beam or the reflected beam to modulate the coherent interference.

30. The method of claim 27 further comprising the step of spatially filtering the reflected beam.

31. The method of claim 27 further comprising the step of optically amplifying the reflected beam in the short arm.

32. The method of claim 27 further comprising the step of adjusting an optical path length of at least one arm of the interferometer.

33. The method of claim 27 further comprising the step of optically detecting the coherent interference.

* * * * *

UNITED STATES PATENT AND TRADEMARK OFFICE
CERTIFICATE OF CORRECTION

PATENT NO. : 6,252,666 B1
DATED : June 26, 2001
INVENTOR(S) : Mandella et al.

Page 1 of 1

It is certified that error appears in the above-identified patent and that said Letters Patent is hereby corrected as shown below:

<u>Title page,</u>
Item [73], change the Assignee to Optical Biopsy Technologies, Inc.

Signed and Sealed this

Twenty-ninth Day of January, 2002

Attest:

Attesting Officer

JAMES E. ROGAN
Director of the United States Patent and Trademark Office